US009290548B2

(12) United States Patent
Levet et al.

(10) Patent No.: US 9,290,548 B2

(45) Date of Patent: Mar. 22, 2016

(54) PROTEINS USED FOR THE DIAGNOSIS OF LYME BORRELIOSIS

(71) Applicant: BIOMERIEUX, Marcy l'Etoile (FR)

(72) Inventors: Lionel Levet, Ouillins (FR); Odile Mejan-Letourneur, Lyons (FR)

(73) Assignee: BIOMERIEUX, Marcy l'Etoile (FR)

( * ) Notice: Subject to any disclaimer, the term of this patent is extended or adjusted under 35 U.S.C. 154(b) by 0 days.

(21) Appl. No.: 14/514,937

(22) Filed: Oct. 15, 2014

(65) Prior Publication Data

US 2015/0037881 A1 Feb. 5, 2015

Related U.S. Application Data

(62) Division of application No. 13/388,168, filed as application No. PCT/FR2010/051787 on Aug. 27, 2010, now Pat. No. 8,895,257.

(30) Foreign Application Priority Data

Aug. 28, 2009 (FR) ..................................... 09 04094

(51) Int. Cl.

*C07H 21/04* (2006.01)
*C07K 14/20* (2006.01)
*C07K 14/195* (2006.01)
*G01N 33/569* (2006.01)
*A61K 39/00* (2006.01)

(52) U.S. Cl.

CPC ............... *C07K 14/20* (2013.01); *C07K 14/195* (2013.01); *G01N 33/56911* (2013.01); *A61K 39/00* (2013.01); *G01N 2333/20* (2013.01); *G01N 2469/20* (2013.01)

(58) Field of Classification Search

None

See application file for complete search history.

(56) References Cited

U.S. PATENT DOCUMENTS

| | | | |
|---|---|---|---|
| 5,620,862 A | 4/1997 | Padula | |
| 6,475,492 B1 | 11/2002 | Philipp et al. | |
| 6,808,711 B2 | 10/2004 | Motz et al. | |
| 2009/0162875 A1 | 6/2009 | Dattwyler et al. | |

FOREIGN PATENT DOCUMENTS

WO WO 00/78800 A2 12/2000

OTHER PUBLICATIONS

Jan. 12, 2011 International Search Report Issued in International Application No. PCT/FR2010/051780.

Jan. 12, 2011 International Search Report Issued in International Application No. PCT/FR2010/051787 (original and English language version).

Jan. 12, 2011 Written Opinion Issued in International Application No. PCT/FR2010/051787 (original and English language version).

Skogman, et al., "Improved Laboratory Diagnostics of Lyme Neuroborreliosis in Children by Detection of Antibodies to New Antigens in Cerebrospinal Fluid," The Pediatric Infectious Disease Journal, (2008), vol. 27, No. 7, pp. 605-612.

Panelius, et al., "Diagnosis of Lyme Neuroborreliosis with Antibodies to Recombinant Proteins DbpA, BBK32, and OspC, and VlsE $IR_6$ Peptide," Journal of Neurology, (2003), vol. 250, No. 11, pp. 1318-1327.

Marangoni, et al. "*Borrelia burgdorferi* VlsE Antigen for the Serological Diagnosis of Lyme Borreliosis," Eur. J. Clin. Microbiol. Infect. Dis., (2008) vol. 27, No. 5, pp. 349-354.

Tjernberg, et al., "Antibody Responses to Borrelia $IR_6$ Peptide Variants and the C6 Peptide in Swedish Patients with Erythema Migrans," International Journal of Medical Microbiology, (2009), vol. 299, No. 6, pp. 439-446.

Steere, et al., "Prospective Study of Serologic Tests for Lyme Disease," Clinical Infectious Diseases, (2008), vol. 47, pp. 188-195.

Göttner, et al., "Heterogeneity of the Immunodominant Surface Protein VlsE among the Three Genospecies of *Borrelia burgdorferi* Pathogenic for Humans," Int. J. Med. Microbiol., (2004), vol. 293, Suppl. 37, pp. 172-173.

Arnaud, et al., "Construction and Expression of a Modular Gene Encoding Bacteriophage T7 RNA Polymerase," Gene, (1997), vol. 199, pp. 149-156.

Bretz, et al., "Specificities and Sensitivities of Four Monoclonal Antibodies for Typing of *Borrelia burgdorferi* Sensu Lato Isolates," Clinical and Diagnostic Laboratory Immunology, (2001), vol. 8, No. 2, pp. 376-384.

Ryffel, et al., "Scored Antibody Reactivity Determined by Immunoblotting Shows an Association between Clinical Manifestations and Presence of *Borrelia burgdorferi* sensu stricto, *B. garinii*, *B. Afzelii*, and *B. Valaisiana* in Humans," Journal of Clinical Microbiology, (1999), vol. 37, No. 12, pp. 4086-4092.

U.S. Appl. No. 13/388,178, Levet et al., filed Jan. 31, 2012.

May 13, 2013 Office Action issued in U.S. Appl. No. 13/388,178.

Greenspan et al. (Nature Biotechnology 7: 936-937, 1999).

Chothia et al. (The EMBO Journal, 1986, 5/4: 823-26).

Mikayama et al. (Nov. 1993, Proc.Natl.Acad.Sci. USA, vol. 90: 10056-10060).

Rudinger et al., (Jun. 1976. Peptide Hormones. Biol. Council. pp. 5-7).

Jan. 30, 2014 Office Action issued in U.S. Appl. No. 13/388,178.

*Primary Examiner* — Jennifer Graser

(74) *Attorney, Agent, or Firm* — Oliff PLC

(57) ABSTRACT

A nucleic acid encoding a chimeric protein, the chimeric protein including (i) at least one amino acid sequence having at least 50% sequence identity with any of the amino acid sequences selected from the group consisting of SEQ ID NOS: 1-5, and (ii) at least one amino acid sequence having at least 80% sequence identity with any of the amino acid sequences selected from the group consisting of SEQ ID NOS: 6-8. The chimeric protein includes at least one amino acid sequence of (i) and at least one amino acid sequence of (ii) that are from different *Borrelia* strains or species.

20 Claims, No Drawings

SEQUENCE LISTING

```
<160> NUMBER OF SEQ ID NOS: 47

<210> SEQ ID NO 1
<211> LENGTH: 274
<212> TYPE: PRT
<213> ORGANISM: Borrelia sp.

<400> SEQUENCE: 1

Lys Asn Asn Val Gly Gly Asp Asp Lys Lys Asp Thr Ala Ala Ser Ile
1               5                   10                  15

Phe Tyr Gln Ser Ile Ile Asn Leu Gly Asn Gly Phe Ile Glu Val Phe
            20                  25                  30

Asn Ala Phe Ser Gly Leu Val Ala Asp Ala Phe Ser Lys Ala Asp Pro
        35                  40                  45

Lys Lys Ser Asp Val Lys Thr Tyr Phe Asp Ser Ile Thr Lys Thr Leu
    50                  55                  60

Lys Asp Thr Lys Thr Lys Leu Glu Asp Ile Ser Lys Glu Lys Thr Gly
65                  70                  75                  80

Gly Glu Lys Thr Pro Ala Val Glu Gly Ile Ala Glu Val Val Lys Thr
                85                  90                  95

Val Gly Glu Trp Leu Asp Gly Leu Ile Lys Ala Ala Glu Gly Gly Gly
            100                 105                 110

Lys Ala Ala Asp Gly Gly Gly Ser Asp Lys Ile Gly Asn Val Ala Ala
        115                 120                 125

Gly Gly Gly Ala Gly Ala Asp Lys Glu Ser Val Asn Gly Ile Ala Gly
    130                 135                 140

Ala Ile Lys Gly Ile Val Glu Ala Ala Lys Lys Val Glu Gly Val Lys
145                 150                 155                 160

Phe Ala Pro Lys Ala Ala Ala Asp Ala Ala Ala Ala Asp Gly Asn Lys
                165                 170                 175

Lys Ala Gly Lys Leu Phe Gly Thr Ala Ala Gly Ala Asp Ala Gly Asp
            180                 185                 190

Val Lys Asp Ala Ala Ala Ala Val Gly Ala Val Ser Gly Glu Gln Ile
        195                 200                 205

Leu Asn Ala Ile Val Thr Ala Ala Gly Gln Ala Gly Gln Ala Gly Lys
    210                 215                 220

Lys Ala Asp Glu Ala Lys Asn Ala Ile Glu Ala Ala Ile Gly Ala Ala
225                 230                 235                 240

Gly Asp Ala Asp Phe Gly Asp Asp Ile Lys Lys Lys Asn Asp Gln Ile
                245                 250                 255

Ala Ala Ala Leu Val Leu Arg Gly Val Ala Lys Asp Gly Lys Phe Ala
            260                 265                 270

Gly Ala


<210> SEQ ID NO 2
<211> LENGTH: 280
<212> TYPE: PRT
<213> ORGANISM: Borrelia sp.

<400> SEQUENCE: 2

Lys Asn Ser Ala Gly Asp Ile Ser Asn Lys Ser Asp Glu Asn Asp Pro
1               5                   10                  15

Thr Thr Leu Phe Tyr Gln Ser Ile Ile Lys Leu Gly Asn Gly Phe Leu
            20                  25                  30

Glu Val Phe Thr Ser Phe Gly Gly Met Val Ala Asp Ala Phe Gly Ala
        35                  40                  45
```

Lys Trp Glu Ala Lys Lys Ser Thr Ile Lys Thr Tyr Phe Asp Thr Met
50 55 60

Ser Gln Lys Leu Glu Glu Thr Lys Lys Gly Leu Glu Lys Leu Ala Asn
65 70 75 80

Asn Gly Glu Glu Ser Glu Ser Glu Asn Lys Ile Gly Asp Ala Val Ala
85 90 95

Ser Thr Ile Lys Glu Val Gly Glu Trp Leu Thr Glu Met Ala Thr Ala
100 105 110

Ala Gly Gly Ala Ala Lys Val Ala Asp Ser Gly Gly Asp Glu Ile Gly
115 120 125

Lys Val Glu Asn Ala Gly Ala Asn Ala Asn Lys Gly Asp Lys Thr Ser
130 135 140

Val Asn Gly Ile Ala Lys Gly Ile Lys Ala Ile Val Gly Val Ala Lys
145 150 155 160

Lys Ala Gly Val Lys Trp Glu Pro Ala Ala Ala Ala Glu Ala Gly Asp
165 170 175

Ala Asn Gly Asn Lys Asn Ala Gly Lys Leu Phe Ala Thr Gly Gly Gln
180 185 190

Gly Asp Ala Ala Ala Gly Lys Glu Ala Ala Leu Ala Val Ser Gly Val
195 200 205

Ser Gly Asp Gln Ile Leu Asn Ala Ile Val Thr Asp Ala Glu Gly Asp
210 215 220

Lys Asn Gly Val Ala Thr Ala Asn Ala Thr Asn Ser Ile Asp Ala Ala
225 230 235 240

Ile Gly Ala Asp Gly Asp Asn Gly Ala Ser Gly Phe Asp Ala Met Lys
245 250 255

Lys Lys Asn Asp Lys Ile Ala Ala Ala Ile Val Leu Arg Gly Met Ala
260 265 270

Lys Asp Gly Lys Phe Ala Val Lys
275 280

<210> SEQ ID NO 3
<211> LENGTH: 284
<212> TYPE: PRT
<213> ORGANISM: Borrelia sp.

<400> SEQUENCE: 3

Lys Asn Asn Ala Glu Leu Ala Glu Ala Glu Ala Lys Asn Gln Ser Ala
1 5 10 15

Lys Asp Phe Tyr His Ala Ile Ile Lys Leu Gly Tyr Gly Phe Val Asp
20 25 30

Val Phe Asn Ala Ile Gly Gly Leu Val Ser Asp Val Phe Tyr Lys Ala
35 40 45

Asp Pro Lys Lys Ser Asp Val Lys Asn Tyr Phe Asp Ser Ile Ala Ser
50 55 60

Ile Leu Lys Glu Thr Gln Thr Lys Leu Asp Ala Leu Ser Lys Glu Gln
65 70 75 80

Gly Gly Gly Asp Gly Gly Thr Gln Val Val Asp Ala Ala Lys Lys Ala
85 90 95

Gly Glu Trp Ile Lys Glu Met His Lys Ala Val Glu Asp Thr Ala Lys
100 105 110

Ala Gly Gly Glu Gly Gly Ser Glu Ser Ile Ala Asn Val Ala Ala Gly
115 120 125

Gly Gly Gly Asn Asp Gly Ala Gly Ala Lys Ala Asp Val Asn Ser Val

-continued

```
    130                 135                 140

Thr Gly Ile Ala Lys Gly Met Lys Ala Ile Val Asp Ala Ala Gly Lys
145                 150                 155                 160

Ala Gly Val Glu Leu Lys Pro Ala Ala Ala Gly Gly Ala Ala Ala Asn
                165                 170                 175

Asp Ala Gly Lys Leu Phe Ala Ser Gly Ala Asn Ala Asn Ala Ala Ala
            180                 185                 190

Asn Ala Asp Asp Ala Glu Gly Ala Ala Glu Ala Ala Gly Lys Ala Val
        195                 200                 205

Ser Ala Val Ser Gly Asp Gln Ile Leu Lys Ala Ile Val Asp Ala Ala
    210                 215                 220

Gly Ala Thr Ala Gly Lys Lys Ala Asn Glu Ala Thr Asn Ala Val Glu
225                 230                 235                 240

Ala Ala Ile Gly Asp Asp Asn Ala Gly Gln Ala Gly Ala Ala Phe Ala
                245                 250                 255

Ala Gly Met Gln Asn Lys Asn Asp Gln Ile Ala Ala Ala Ile Val Leu
            260                 265                 270

Arg Gly Leu Ala Lys Ser Gly Lys Phe Ala Asn Glu
        275                 280


<210> SEQ ID NO 4
<211> LENGTH: 279
<212> TYPE: PRT
<213> ORGANISM: Borrelia sp.

<400> SEQUENCE: 4

Lys Asn Asn Ala Val Gly Lys Gly Asn Asp Asp Lys Asp Ser Val Lys
1               5                   10                  15

Thr Phe Tyr Glu Ser Ile Ile Asn Leu Gly Asn Gly Phe Ile Asp Val
            20                  25                  30

Phe Asn Ala Phe Ser Gly Leu Val Ala Asp Thr Phe Phe Lys Ser Asp
        35                  40                  45

Pro Lys Lys Ser Asp Val Lys Thr Tyr Phe Glu Ser Ile Ser Ser Thr
    50                  55                  60

Leu Lys Ala Thr Lys Gly Lys Leu Asp Glu Leu Val Ser Ala Lys Lys
65                  70                  75                  80

Gly Glu Gly Gly Ser Val Lys Ala Ser Val Glu Ser Ala Val Asp Glu
                85                  90                  95

Val Ser Lys Trp Leu Glu Glu Met Ile Lys Ala Ala Glu Glu Ala Ala
            100                 105                 110

Lys Val Gly Gly Thr Gly Gly Asp Gly Lys Ile Gly Asp Ser Ala Ala
        115                 120                 125

Asn His Gly Ala Lys Ala Asp Lys Asp Ser Val Lys Gly Ile Ala Lys
    130                 135                 140

Gly Ile Lys Gly Ile Val Asp Ala Ala Gly Lys Ala Leu Gly Glu Lys
145                 150                 155                 160

Gly Ala Leu Lys Asp Val Lys Ala Ala Ala Asp Asp Glu Ala Asn Ala
                165                 170                 175

Asp Ala Gly Lys Leu Phe Ala Gly Asn Ala Asn Ala Ala Val Gly Ala
            180                 185                 190

Ala Ala Asp Ile Ala Lys Ala Ala Gly Ala Val Thr Ala Val Ser Gly
        195                 200                 205

Glu Gln Ile Leu Lys Ala Ile Val Glu Ala Ala Gly Asp Pro Ala Asn
    210                 215                 220
```

-continued

```
Gln Ala Gly Lys Lys Ala Glu Glu Ala Lys Asn Pro Ile Ala Ala Ala
225                 230                 235                 240

Ile Gly Thr Asp Asp Asp Asn Gly Ala Ala Phe Lys Asp Glu Met Lys
                245                 250                 255

Lys Ser Asp Lys Ile Ala Ala Ala Ile Val Leu Arg Gly Val Ala Lys
            260                 265                 270

Asp Gly Lys Phe Ala Val Lys
        275


<210> SEQ ID NO 5
<211> LENGTH: 279
<212> TYPE: PRT
<213> ORGANISM: Borrelia sp.

<400> SEQUENCE: 5

Lys Ser Gln Val Ala Asp Lys Asp Asp Pro Thr Asn Lys Phe Tyr Gln
1               5                   10                  15

Ser Val Ile Gln Leu Gly Asn Gly Phe Leu Asp Val Phe Thr Ser Phe
            20                  25                  30

Gly Gly Leu Val Ala Glu Ala Phe Gly Phe Lys Ser Asp Pro Lys Lys
        35                  40                  45

Ser Asp Val Lys Thr Tyr Phe Thr Thr Val Ala Ala Lys Leu Glu Lys
    50                  55                  60

Thr Lys Thr Asp Leu Asn Ser Leu Pro Lys Glu Lys Ser Asp Ile Ser
65                  70                  75                  80

Ser Thr Thr Gly Lys Pro Asp Ser Thr Gly Ser Val Gly Thr Ala Val
                85                  90                  95

Glu Gly Ala Ile Lys Glu Val Ser Glu Leu Leu Asp Lys Leu Val Lys
            100                 105                 110

Ala Val Lys Thr Ala Glu Gly Ala Ser Ser Gly Thr Ala Ala Ile Gly
        115                 120                 125

Glu Val Val Ala Asp Ala Asp Ala Ala Lys Val Ala Asp Lys Ala Ser
    130                 135                 140

Val Lys Gly Ile Ala Lys Gly Ile Lys Glu Ile Val Glu Ala Ala Gly
145                 150                 155                 160

Gly Ser Glu Lys Leu Lys Ala Val Ala Ala Ala Lys Gly Glu Asn Asn
                165                 170                 175

Lys Gly Ala Gly Lys Leu Phe Gly Lys Ala Gly Ala Ala Ala His Gly
            180                 185                 190

Asp Ser Glu Ala Ala Ser Lys Ala Ala Gly Ala Val Ser Ala Val Ser
        195                 200                 205

Gly Glu Gln Ile Leu Ser Ala Ile Val Thr Ala Ala Asp Ala Ala Glu
    210                 215                 220

Gln Asp Gly Lys Lys Pro Glu Glu Ala Lys Asn Pro Ile Ala Ala Ala
225                 230                 235                 240

Ile Gly Asp Lys Asp Gly Gly Ala Glu Phe Gly Gln Asp Glu Met Lys
                245                 250                 255

Lys Asp Asp Gln Ile Ala Ala Ala Ile Ala Leu Arg Gly Met Ala Lys
            260                 265                 270

Asp Gly Lys Phe Ala Val Lys
        275


<210> SEQ ID NO 6
<211> LENGTH: 25
<212> TYPE: PRT
<213> ORGANISM: Borrelia sp.
```

-continued

<400> SEQUENCE: 6

Met Lys Lys Asp Asp Gln Ile Ala Ala Ala Ile Ala Leu Arg Gly Met
1 5 10 15

Ala Lys Asp Gly Lys Phe Ala Val Lys
20 25

<210> SEQ ID NO 7
<211> LENGTH: 17
<212> TYPE: PRT
<213> ORGANISM: Borrelia sp.

<400> SEQUENCE: 7

Ile Val Ala Ala Ile Val Leu Arg Gly Val Ala Lys Ser Gly Lys Phe
1 5 10 15

Ala

<210> SEQ ID NO 8
<211> LENGTH: 25
<212> TYPE: PRT
<213> ORGANISM: Borrelia sp.

<400> SEQUENCE: 8

Met Lys Lys Asp Asp Gln Ile Ala Ala Ala Met Val Leu Arg Gly Met
1 5 10 15

Ala Lys Asp Gly Gln Phe Ala Leu Lys
20 25

<210> SEQ ID NO 9
<211> LENGTH: 7
<212> TYPE: PRT
<213> ORGANISM: Borrelia sp.

<400> SEQUENCE: 9

Asp Gly Glu Lys Glu Lys Ala
1 5

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct - Tag His

<400> SEQUENCE: 10

His His His His His His
1 5

<210> SEQ ID NO 11
<211> LENGTH: 18
<212> TYPE: DNA
<213> ORGANISM: Artificial Sequence
<220> FEATURE:
<223> OTHER INFORMATION: Synthetic Construct - DNA Tag His

<400> SEQUENCE: 11
catcatcatc atcatcat 18

<210> SEQ ID NO 12
<211> LENGTH: 18
<212> TYPE: DNA
<213> ORGANISM: Artificial Sequence
<220> FEATURE:
<223> OTHER INFORMATION: Synthetic Construct - DNA Tag His -continued

<400> SEQUENCE: 12
catcatcatc atcatcac 18

<210> SEQ ID NO 13
<211> LENGTH: 18
<212> TYPE: DNA
<213> ORGANISM: Artificial Sequence
<220> FEATURE:
<223> OTHER INFORMATION: Synthetic Construct - DNA Tag His

<400> SEQUENCE: 13
catcatcacc accatcat 18

<210> SEQ ID NO 14
<211> LENGTH: 4
<212> TYPE: PRT
<213> ORGANISM: Artificial Sequence
<220> FEATURE:
<223> OTHER INFORMATION: Synthetic Construct - aa+

<400> SEQUENCE: 14

Met Arg Gly Ser
1

<210> SEQ ID NO 15
<211> LENGTH: 12
<212> TYPE: DNA
<213> ORGANISM: Artificial Sequence
<220> FEATURE:
<223> OTHER INFORMATION: Synthetic Construct - DNA aa+

<400> SEQUENCE: 15
atgaggggat cc 12

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct - Tag His 3

<400> SEQUENCE: 16

His His His His His His His His
1 5

<210> SEQ ID NO 17
<211> LENGTH: 24
<212> TYPE: DNA
<213> ORGANISM: Artificial Sequence
<220> FEATURE:
<223> OTHER INFORMATION: Synthetic Construct - DNA Tag His

<400> SEQUENCE: 17
catcatcatc atcatcatca tcat 24

<210> SEQ ID NO 18
<211> LENGTH: 2
<212> TYPE: PRT
<213> ORGANISM: Artificial Sequence
<220> FEATURE:
<223> OTHER INFORMATION: Synthetic Construct - aa+ 1

<400> SEQUENCE: 18

Met Gly
1

-continued

<210> SEQ ID NO 19
<211> LENGTH: 6
<212> TYPE: DNA
<213> ORGANISM: Artificial Sequence
<220> FEATURE:
<223> OTHER INFORMATION: Synthetic Construct - DNA aa+ 1

<400> SEQUENCE: 19 atgggc 6

<210> SEQ ID NO 20
<211> LENGTH: 348
<212> TYPE: PRT
<213> ORGANISM: Borrelia sp.

<400> SEQUENCE: 20

```
Lys Asn Asn Val Gly Gly Asp Asp Lys Lys Asp Thr Ala Ala Ser Ile
1               5                   10                  15

Phe Tyr Gln Ser Ile Ile Asn Leu Gly Asn Gly Phe Ile Glu Val Phe
            20                  25                  30

Asn Ala Phe Ser Gly Leu Val Ala Asp Ala Phe Ser Lys Ala Asp Pro
        35                  40                  45

Lys Lys Ser Asp Val Lys Thr Tyr Phe Asp Ser Ile Thr Lys Thr Leu
    50                  55                  60

Lys Asp Thr Lys Thr Lys Leu Glu Asp Ile Ser Lys Glu Lys Thr Gly
65                  70                  75                  80

Gly Glu Lys Thr Pro Ala Val Glu Gly Ile Ala Glu Val Val Lys Thr
                85                  90                  95

Val Gly Glu Trp Leu Asp Gly Leu Ile Lys Ala Ala Glu Gly Gly Gly
            100                 105                 110

Lys Ala Ala Asp Gly Gly Gly Ser Asp Lys Ile Gly Asn Val Ala Ala
        115                 120                 125

Gly Gly Gly Ala Gly Ala Asp Lys Glu Ser Val Asn Gly Ile Ala Gly
    130                 135                 140

Ala Ile Lys Gly Ile Val Glu Ala Ala Lys Lys Val Glu Gly Val Lys
145                 150                 155                 160

Phe Ala Pro Lys Ala Ala Ala Asp Ala Ala Ala Ala Asp Gly Asn Lys
                165                 170                 175

Lys Ala Gly Lys Leu Phe Gly Thr Ala Ala Gly Ala Asp Ala Gly Asp
            180                 185                 190

Val Lys Asp Ala Ala Ala Ala Val Gly Ala Val Ser Gly Glu Gln Ile
        195                 200                 205

Leu Asn Ala Ile Val Thr Ala Ala Gly Gln Ala Gly Gln Ala Gly Lys
    210                 215                 220

Lys Ala Asp Glu Ala Lys Asn Ala Ile Glu Ala Ala Ile Gly Ala Ala
225                 230                 235                 240

Gly Asp Ala Asp Phe Gly Asp Asp Ile Lys Lys Lys Asn Asp Gln Ile
                245                 250                 255

Ala Ala Ala Leu Val Leu Arg Gly Val Ala Lys Asp Gly Lys Phe Ala
            260                 265                 270

Gly Ala Met Lys Lys Asp Asp Gln Ile Ala Ala Ala Ile Ala Leu Arg
        275                 280                 285

Gly Met Ala Lys Asp Gly Lys Phe Ala Val Lys Asp Gly Glu Lys Glu
    290                 295                 300

Lys Ala Ile Val Ala Ala Ile Val Leu Arg Gly Val Ala Lys Ser Gly
```

-continued

```
305                 310                 315                 320

Lys Phe Ala Met Lys Lys Asp Asp Gln Ile Ala Ala Ala Met Val Leu
                325                 330                 335

Arg Gly Met Ala Lys Asp Gly Gln Phe Ala Leu Lys
            340                 345


<210> SEQ ID NO 21
<211> LENGTH: 358
<212> TYPE: PRT
<213> ORGANISM: Borrelia sp.

<400> SEQUENCE: 21

Met Arg Gly Ser His His His His His His Lys Asn Asn Val Gly Gly
1               5                   10                  15

Asp Asp Lys Lys Asp Thr Ala Ala Ser Ile Phe Tyr Gln Ser Ile Ile
            20                  25                  30

Asn Leu Gly Asn Gly Phe Ile Glu Val Phe Asn Ala Phe Ser Gly Leu
        35                  40                  45

Val Ala Asp Ala Phe Ser Lys Ala Asp Pro Lys Lys Ser Asp Val Lys
    50                  55                  60

Thr Tyr Phe Asp Ser Ile Thr Lys Thr Leu Lys Asp Thr Lys Thr Lys
65                  70                  75                  80

Leu Glu Asp Ile Ser Lys Glu Lys Thr Gly Gly Glu Lys Thr Pro Ala
                85                  90                  95

Val Glu Gly Ile Ala Glu Val Val Lys Thr Val Gly Glu Trp Leu Asp
            100                 105                 110

Gly Leu Ile Lys Ala Ala Glu Gly Gly Gly Lys Ala Ala Asp Gly Gly
        115                 120                 125

Gly Ser Asp Lys Ile Gly Asn Val Ala Ala Gly Gly Gly Ala Gly Ala
    130                 135                 140

Asp Lys Glu Ser Val Asn Gly Ile Ala Gly Ala Ile Lys Gly Ile Val
145                 150                 155                 160

Glu Ala Ala Lys Lys Val Glu Gly Val Lys Phe Ala Pro Lys Ala Ala
                165                 170                 175

Ala Asp Ala Ala Ala Ala Asp Gly Asn Lys Lys Ala Gly Lys Leu Phe
            180                 185                 190

Gly Thr Ala Ala Gly Ala Asp Ala Gly Asp Val Lys Asp Ala Ala Ala
        195                 200                 205

Ala Val Gly Ala Val Ser Gly Glu Gln Ile Leu Asn Ala Ile Val Thr
    210                 215                 220

Ala Ala Gly Gln Ala Gly Gln Ala Gly Lys Lys Ala Asp Glu Ala Lys
225                 230                 235                 240

Asn Ala Ile Glu Ala Ala Ile Gly Ala Ala Gly Asp Ala Asp Phe Gly
                245                 250                 255

Asp Asp Ile Lys Lys Lys Asn Asp Gln Ile Ala Ala Ala Leu Val Leu
            260                 265                 270

Arg Gly Val Ala Lys Asp Gly Lys Phe Ala Gly Ala Met Lys Lys Asp
        275                 280                 285

Asp Gln Ile Ala Ala Ala Ile Ala Leu Arg Gly Met Ala Lys Asp Gly
    290                 295                 300

Lys Phe Ala Val Lys Asp Gly Glu Lys Glu Lys Ala Ile Val Ala Ala
305                 310                 315                 320

Ile Val Leu Arg Gly Val Ala Lys Ser Gly Lys Phe Ala Met Lys Lys
                325                 330                 335
```

-continued

```
Asp Asp Gln Ile Ala Ala Ala Met Val Leu Arg Gly Met Ala Lys Asp
            340                 345                 350

Gly Gln Phe Ala Leu Lys
        355


<210> SEQ ID NO 22
<211> LENGTH: 1077
<212> TYPE: DNA
<213> ORGANISM: Borrelia sp.

<400> SEQUENCE: 22

atgaggggat cccaccacca ccatcatcat aaaaataatg tcggcggcga tgacaaaaaa      60

gatactgcgg ccagcatctt ctaccagtct attattaacc tgggtaacgg gttcattgaa     120

gtgtttaatg ccttttccgg gctggtggcc gacgcgttta gcaaagcaga tccgaaaaaa     180

tcagatgtca aaacttactt cgattcgatc acgaaaacac tgaaagatac caaaactaag     240

ctggaagata ttagcaaaga aaaaacgggc ggcgaaaaaa cgccagccgt tgaaggtatc     300

gccgaagtcg tgaaaaccgt gggagagtgg ctggatggcc tgattaaagc ggcggaaggg     360

ggcggcaaag cggcggatgg tggcggttcg gacaaaattg ggaatgtcgc tgcaggcggc     420

ggcgcgggcg ccgacaagga aagtgtgaat ggaatcgcag gtgccattaa aggtatcgtg     480

gaagctgcaa aaaaggtgga aggtgtgaaa ttcgccccga aagctgcggc ggatgcagcc     540

gccgctgatg gtaacaaaaa agcaggcaaa ctgtttggta ccgcggcggg cgcagacgcg     600

ggagacgtga aagatgcagc cgctgcggta ggggccgtga gcggtgaaca gattctgaat     660

gcgattgtta cggcggcggg ccaggcaggc caggcgggga aaaaagctga tgaagcaaaa     720

aatgcgattg aagctgccat tggtgcggct ggcgatgcgg attttggtga cgacattaaa     780

aagaaaaacg atcaaattgc ggcggcgctg gttctgcgcg gagttgctaa agacggcaaa     840

tttgccggcg ctatgaagaa agacgaccaa atcgcggcag ccattgcgct gcgcggcatg     900

gcgaaagacg gcaaatttgc ggtgaaagat ggcgaaaaag aaaaagcgat tgtggcggcg     960

atcgttctgc gcggtgttgc gaaaagcggt aaattcgcga tgaaaaaaga tgatcagatc    1020

gccgcagcga tggttctgcg tggtatggcc aaagatggtc agtttgccct gaaataa       1077


<210> SEQ ID NO 23
<211> LENGTH: 357
<212> TYPE: PRT
<213> ORGANISM: Borrelia sp.

<400> SEQUENCE: 23

Met Gly His His His His His His His His Lys Asn Asn Val Gly Gly
1               5                   10                  15

Asp Asp Lys Lys Asp Thr Ala Ala Ser Ile Phe Tyr Gln Ser Ile Ile
            20                  25                  30

Asn Leu Gly Asn Gly Phe Ile Glu Val Phe Asn Ala Phe Ser Gly Leu
        35                  40                  45

Val Ala Asp Ala Phe Ser Lys Ala Asp Pro Lys Lys Ser Asp Val Lys
    50                  55                  60

Thr Tyr Phe Asp Ser Ile Thr Lys Thr Leu Lys Asp Thr Lys Thr Lys
65                  70                  75                  80

Leu Glu Asp Ile Ser Lys Glu Lys Thr Gly Gly Glu Lys Thr Pro Ala
                85                  90                  95

Val Glu Gly Ile Ala Glu Val Val Lys Thr Val Gly Glu Trp Leu Asp
            100                 105                 110
```

```
Gly Leu Ile Lys Ala Ala Glu Gly Gly Gly Lys Ala Ala Asp Gly Gly
        115                 120                 125

Gly Ser Asp Lys Ile Gly Asn Val Ala Ala Gly Gly Gly Ala Gly Ala
    130                 135                 140

Asp Lys Glu Ser Val Asn Gly Ile Ala Gly Ala Ile Lys Gly Ile Val
145                 150                 155                 160

Glu Ala Ala Lys Lys Val Glu Gly Val Lys Phe Ala Pro Lys Ala Ala
                165                 170                 175

Ala Asp Ala Ala Ala Ala Asp Gly Asn Lys Lys Ala Gly Lys Leu Phe
            180                 185                 190

Gly Thr Ala Ala Gly Ala Asp Ala Gly Asp Val Lys Asp Ala Ala Ala
        195                 200                 205

Ala Val Gly Ala Val Ser Gly Glu Gln Ile Leu Asn Ala Ile Val Thr
    210                 215                 220

Ala Gly Gln Ala Gly Gln Ala Gly Lys Lys Ala Asp Glu Ala Lys Asn
225                 230                 235                 240

Ala Ile Glu Ala Ala Ile Gly Ala Ala Gly Asp Ala Asp Phe Gly Asp
                245                 250                 255

Asp Ile Lys Lys Lys Asn Asp Gln Ile Ala Ala Ala Leu Val Leu Arg
            260                 265                 270

Gly Val Ala Lys Asp Gly Lys Phe Ala Gly Ala Met Lys Lys Asp Asp
        275                 280                 285

Gln Ile Ala Ala Ala Ile Ala Leu Arg Gly Met Ala Lys Asp Gly Lys
    290                 295                 300

Phe Ala Val Lys Asp Gly Glu Lys Glu Lys Ala Ile Val Ala Ala Ile
305                 310                 315                 320

Val Leu Arg Gly Val Ala Lys Ser Gly Lys Phe Ala Met Lys Lys Asp
                325                 330                 335

Asp Gln Ile Ala Ala Ala Met Val Leu Arg Gly Met Ala Lys Asp Gly
            340                 345                 350

Gln Phe Ala Leu Lys
        355


<210> SEQ ID NO 24
<211> LENGTH: 1074
<212> TYPE: DNA
<213> ORGANISM: Borrelia sp.

<400> SEQUENCE: 24

atgggccatc atcatcatca tcatcatcat aaaaacaacg tgggcggcga tgataaaaaa      60

gataccgcgg cgagcatttt ttatcagagc attattaacc tgggcaacgg ctttattgaa     120

gtgtttaacg cgtttagcgg cctggtggcg gatgcgttta gcaaagcgga tccgaaaaaa     180

agcgatgtga aaacctattt tgatagcatt accaaaaccc tgaaagatac caaaaccaaa     240

ctggaagata ttagcaaaga aaaaaccggc ggcgaaaaaa ccccggcggt ggaaggcatt     300

gcggaagtgg tgaaaaccgt gggcgaatgg ctggatggcc tgattaaagc ggcggaaggc     360

ggcggcaaag cggcggatgg cggcggcagc gataaaattg gcaacgtggc ggcgggcggc     420

ggcgcgggcg cggataaaga aagcgtgaac ggcattgcgg gcgcgattaa aggcattgtg     480

gaagcggcga aaaaagtgga aggcgtgaaa tttgcgccga aagcggcggc ggatgcggcg     540

gcggcggatg gcaacaaaaa agcgggcaaa ctgtttggca ccgcggcggg cgcggatgcg     600

ggcgatgtga aagatgcggc ggcggcggtg ggcgcggtga gcggcgaaca gattctgaac     660

gcgattgtga ccgcgggcca ggcgggccag gcgggcaaaa aagcggatga agcgaaaaac     720
```

-continued

```
gcgattgaag cggcgattgg cgcggcgggc gatgcggatt ttggcgatga tattaaaaaa    780

aaaaacgatc agattgcggc ggcgctggtg ctgcgcggcg tggcgaaaga tggcaaattt    840

gcgggcgcga tgaaaaaaga tgatcagatt gcggcggcga ttgcgctgcg cggcatggcg    900

aaagatggca aatttgcggt gaaagatggc gaaaaagaaa aagcgattgt ggcggcgatt    960

gtgctgcgcg gcgtggcgaa aagcggcaaa tttgcgatga aaaaagatga tcagattgcg   1020

gcggcgatgg tgctgcgcgg catggcgaaa gatggccagt ttgcgctgaa ataa         1074
```

<210> SEQ ID NO 25
<211> LENGTH: 149
<212> TYPE: PRT
<213> ORGANISM: Borrelia sp.

<400> SEQUENCE: 25

```
Ser Leu Thr Gly Lys Ala Arg Leu Glu Ser Ser Val Lys Asp Ile Thr
1               5                   10                  15

Asn Glu Ile Glu Lys Ala Ile Lys Glu Ala Glu Asp Ala Gly Val Lys
            20                  25                  30

Thr Asp Ala Phe Thr Glu Thr Gln Thr Gly Gly Lys Val Ala Gly Pro
        35                  40                  45

Lys Ile Arg Ala Ala Lys Ile Arg Val Ala Asp Leu Thr Ile Lys Phe
    50                  55                  60

Leu Glu Ala Thr Glu Glu Glu Thr Ile Thr Phe Lys Glu Asn Gly Ala
65                  70                  75                  80

Gly Glu Asp Glu Phe Ser Gly Ile Tyr Asp Leu Ile Leu Asn Ala Ala
                85                  90                  95

Lys Ala Val Glu Lys Ile Gly Met Lys Asp Met Thr Lys Thr Val Glu
            100                 105                 110

Glu Ala Ala Lys Glu Asn Pro Lys Thr Thr Ala Asn Gly Ile Ile Glu
        115                 120                 125

Ile Val Lys Val Met Lys Ala Lys Val Glu Asn Ile Lys Glu Lys Gln
    130                 135                 140

Thr Lys Asn Gln Lys
145
```

<210> SEQ ID NO 26
<211> LENGTH: 211
<212> TYPE: PRT
<213> ORGANISM: Borrelia sp.

<400> SEQUENCE: 26

```
Lys Lys Asn Thr Leu Ser Ala Ile Leu Met Thr Leu Phe Leu Phe Ile
1               5                   10                  15

Ser Cys Asn Asn Ser Gly Lys Gly Gly Asp Ser Ala Ser Thr Asn Pro
            20                  25                  30

Ala Asp Glu Ser Ala Lys Gly Pro Asn Leu Thr Glu Ile Ser Lys Lys
        35                  40                  45

Ile Thr Asp Ser Asn Ala Phe Val Leu Ala Val Lys Glu Val Glu Thr
    50                  55                  60

Leu Val Leu Ser Ile Asp Glu Leu Ala Lys Lys Ala Ile Gly Gln Lys
65                  70                  75                  80

Ile Asp Asn Asn Asn Gly Leu Ala Ala Leu Asn Asn Gln Asn Gly Ser
                85                  90                  95

Leu Leu Ala Gly Ala Tyr Ala Ile Ser Thr Leu Ile Thr Glu Lys Leu
            100                 105                 110
```

-continued

```
Ser Lys Leu Lys Asn Leu Glu Glu Leu Lys Thr Glu Ile Ala Lys Ala
        115                 120                 125

Lys Lys Cys Ser Glu Glu Phe Thr Asn Lys Leu Lys Ser Gly His Ala
    130                 135                 140

Asp Leu Gly Lys Gln Asp Ala Thr Asp Asp His Ala Lys Ala Ala Ile
145                 150                 155                 160

Leu Lys Thr His Ala Thr Thr Asp Lys Gly Ala Lys Glu Phe Lys Asp
                165                 170                 175

Leu Phe Glu Ser Val Glu Gly Leu Leu Lys Ala Ala Gln Val Ala Leu
            180                 185                 190

Thr Asn Ser Val Lys Glu Leu Thr Ser Pro Val Val Ala Glu Ser Pro
        195                 200                 205

Lys Lys Pro
    210


<210> SEQ ID NO 27
<211> LENGTH: 164
<212> TYPE: PRT
<213> ORGANISM: Borrelia sp.

<400> SEQUENCE: 27

Thr Gly Ala Thr Lys Ile Arg Leu Glu Arg Ser Ala Lys Asp Ile Thr
1               5                   10                  15

Asp Glu Ile Asp Ala Ile Lys Lys Asp Ala Ala Leu Lys Gly Val Asn
            20                  25                  30

Phe Asp Ala Phe Lys Asp Lys Lys Thr Gly Ser Gly Val Ser Glu Asn
        35                  40                  45

Pro Phe Ile Leu Glu Ala Lys Val Arg Ala Thr Thr Val Ala Glu Lys
    50                  55                  60

Phe Val Ile Ala Ile Glu Glu Glu Ala Thr Lys Leu Lys Glu Thr Gly
65                  70                  75                  80

Ser Ser Gly Glu Phe Ser Ala Met Tyr Asp Leu Met Phe Glu Val Ser
                85                  90                  95

Lys Pro Leu Gln Lys Leu Gly Ile Gln Glu Met Thr Lys Thr Val Ser
            100                 105                 110

Asp Ala Ala Glu Glu Asn Pro Pro Thr Thr Ala Gln Gly Val Leu Glu
        115                 120                 125

Ile Ala Lys Lys Met Arg Glu Lys Leu Gln Arg Val His Thr Lys Asn
    130                 135                 140

Tyr Cys Thr Leu Lys Lys Lys Glu Asn Ser Thr Phe Thr Asp Glu Lys
145                 150                 155                 160

Cys Lys Asn Asn


<210> SEQ ID NO 28
<211> LENGTH: 185
<212> TYPE: PRT
<213> ORGANISM: Borrelia sp.

<400> SEQUENCE: 28

Asn Thr Ser Ala Asn Ser Ala Asp Glu Ser Val Lys Gly Pro Asn Leu
1               5                   10                  15

Thr Glu Ile Ser Lys Lys Ile Thr Asp Ser Asn Ala Val Leu Leu Ala
            20                  25                  30

Val Lys Glu Val Glu Ala Leu Leu Ser Ser Ile Asp Glu Ile Ala Ala
        35                  40                  45
```

```
Lys Ala Ile Gly Lys Lys Ile His Gln Asn Asn Gly Leu Asp Thr Glu
    50                  55                  60

Asn Asn His Asn Gly Ser Leu Leu Ala Gly Ala Tyr Ala Ile Ser Thr
65                  70                  75                  80

Leu Ile Lys Gln Lys Leu Asp Gly Leu Lys Asn Glu Gly Leu Lys Glu
                85                  90                  95

Lys Ile Asp Ala Ala Lys Lys Cys Ser Glu Thr Phe Thr Asn Lys Leu
            100                 105                 110

Lys Glu Lys His Thr Asp Ser Phe Gly Lys Glu Gly Val Thr Asp Ala
        115                 120                 125

Asp Ala Lys Glu Ala Ile Leu Lys Thr Asn Gly Thr Lys Thr Lys Gly
    130                 135                 140

Ala Glu Glu Leu Gly Lys Leu Phe Glu Ser Val Glu Val Leu Ser Lys
145                 150                 155                 160

Ala Ala Lys Glu Met Leu Ala Asn Ser Val Lys Glu Leu Thr Ser Pro
                165                 170                 175

Val Val Ala Glu Ser Pro Lys Lys Pro
            180                 185


<210> SEQ ID NO 29
<211> LENGTH: 162
<212> TYPE: PRT
<213> ORGANISM: Borrelia sp.

<400> SEQUENCE: 29

Thr Gly Glu Thr Lys Ile Arg Leu Glu Ser Ser Ala Gln Glu Ile Lys
1               5                   10                  15

Asp Glu Ile Asn Lys Ile Lys Ala Asn Ala Lys Lys Glu Gly Val Lys
            20                  25                  30

Phe Glu Ala Phe Thr Asp Lys Gln Thr Gly Ser Lys Val Ser Glu Lys
        35                  40                  45

Pro Glu Phe Ile Leu Lys Ala Lys Ile Lys Ala Ile Gln Val Ala Glu
    50                  55                  60

Lys Phe Val Lys Ala Ile Lys Glu Glu Ala Glu Lys Leu Lys Lys Ser
65                  70                  75                  80

Gly Ser Ser Gly Ala Phe Ser Ala Met Tyr Asp Leu Met Leu Asp Val
                85                  90                  95

Ser Lys Pro Leu Glu Glu Ile Gly Ile Gln Lys Met Thr Gly Thr Val
            100                 105                 110

Thr Lys Glu Ala Glu Lys Thr Pro Pro Thr Thr Ala Glu Gly Ile Leu
        115                 120                 125

Ala Ile Ala Gln Ala Met Glu Glu Lys Leu Asn Asn Val Asn Lys Lys
    130                 135                 140

Gln Gln Asp Ala Leu Lys Asn Leu Glu Glu Lys Ala Asn Thr Ala Ala
145                 150                 155                 160

Thr Thr


<210> SEQ ID NO 30
<211> LENGTH: 154
<212> TYPE: PRT
<213> ORGANISM: Borrelia sp.

<400> SEQUENCE: 30

Ser Gly Thr Gly Lys Ala Arg Leu Glu Ser Ser Val Lys Asp Ile Thr
1               5                   10                  15

Asp Glu Ile Asp Lys Ala Ile Lys Glu Ala Ile Ala Asp Gly Val Lys
```

-continued

```
            20                  25                  30

Leu Asn Glu Leu Glu Glu Asn Lys Thr Gly Ala Lys Lys Gly Gly Pro
        35                  40                  45

Gln Ile Arg Asp Ala Lys Ile Arg Val Ile Asn Leu Ser Val Lys Phe
    50                  55                  60

Leu Lys Glu Ile Glu Glu Glu Ala Asn Ile Leu Lys Asp Asn Val Gly
65                  70                  75                  80

Met Asn Lys Val Asp Lys Asp Gln Leu Leu Lys Asp Met Tyr Asp Leu
                85                  90                  95

Met Leu Asn Ala Ala Gly Ser Leu Gln Lys Leu Gly Leu Gln Glu Met
            100                 105                 110

Ile Lys Thr Val Thr Gln Ala Ala Glu Lys Thr Pro Pro Thr Thr Val
        115                 120                 125

Glu Gly Ile Leu Met Ile Ala Asn Thr Ile Glu Asp Lys Leu Lys Lys
    130                 135                 140

Ile Lys Gly Lys Gln Glu Thr Asn Lys Lys
145                 150


<210> SEQ ID NO 31
<211> LENGTH: 176
<212> TYPE: PRT
<213> ORGANISM: Borrelia sp.

<400> SEQUENCE: 31

Asp Glu Ser Ala Lys Gly Pro Asn Leu Thr Val Ile Ser Lys Lys Ile
1               5                   10                  15

Thr Asp Ser Asn Ala Phe Leu Leu Ala Val Lys Glu Val Glu Ala Leu
            20                  25                  30

Leu Ser Ser Ile Asp Glu Leu Ser Lys Ala Ile Gly Lys Lys Ile Lys
        35                  40                  45

Asn Asp Gly Thr Leu Asp Asn Glu Ala Asn Arg Asn Glu Ser Leu Ile
    50                  55                  60

Ala Gly Ala Tyr Glu Ile Ser Lys Leu Ile Thr Gln Lys Leu Ser Val
65                  70                  75                  80

Leu Asn Ser Glu Glu Leu Lys Glu Lys Ile Lys Glu Ala Lys Asp Cys
                85                  90                  95

Ser Glu Lys Phe Thr Thr Lys Leu Lys Asp Ser His Ala Glu Leu Gly
            100                 105                 110

Ile Gln Ser Val Gln Asp Asp Asn Ala Lys Lys Ala Ile Leu Lys Thr
        115                 120                 125

His Gly Thr Lys Asp Lys Gly Ala Lys Glu Leu Glu Glu Leu Phe Lys
    130                 135                 140

Ser Leu Glu Ser Leu Ser Lys Ala Ala Gln Ala Ala Leu Thr Asn Ser
145                 150                 155                 160

Val Lys Glu Leu Thr Asn Pro Val Val Ala Glu Ser Pro Lys Lys Pro
                165                 170                 175


<210> SEQ ID NO 32
<211> LENGTH: 361
<212> TYPE: PRT
<213> ORGANISM: Borrelia sp.

<400> SEQUENCE: 32

Met Ser Leu Thr Gly Lys Ala Arg Leu Glu Ser Ser Val Lys Asp Ile
1               5                   10                  15

Thr Asn Glu Ile Glu Lys Ala Ile Lys Glu Ala Glu Asp Ala Gly Val
```

-continued

```
            20                  25                  30

Lys Thr Asp Ala Phe Thr Glu Thr Gln Thr Gly Gly Lys Val Ala Gly
        35                  40                  45

Pro Lys Ile Arg Ala Ala Lys Ile Arg Val Ala Asp Leu Thr Ile Lys
    50                  55                  60

Phe Leu Glu Ala Thr Glu Glu Glu Thr Ile Thr Phe Lys Glu Asn Gly
65                  70                  75                  80

Ala Gly Glu Asp Glu Phe Ser Gly Ile Tyr Asp Leu Ile Leu Asn Ala
                85                  90                  95

Ala Lys Ala Val Glu Lys Ile Gly Met Lys Asp Met Thr Lys Thr Val
            100                 105                 110

Glu Glu Ala Ala Lys Glu Asn Pro Lys Thr Thr Ala Asn Gly Ile Ile
        115                 120                 125

Glu Ile Val Lys Val Met Lys Ala Lys Val Glu Asn Ile Lys Glu Lys
    130                 135                 140

Gln Thr Lys Asn Gln Lys Lys Lys Asn Thr Leu Ser Ala Ile Leu Met
145                 150                 155                 160

Thr Leu Phe Leu Phe Ile Ser Cys Asn Asn Ser Gly Lys Gly Gly Asp
                165                 170                 175

Ser Ala Ser Thr Asn Pro Ala Asp Glu Ser Ala Lys Gly Pro Asn Leu
            180                 185                 190

Thr Glu Ile Ser Lys Lys Ile Thr Asp Ser Asn Ala Phe Val Leu Ala
        195                 200                 205

Val Lys Glu Val Glu Thr Leu Val Leu Ser Ile Asp Glu Leu Ala Lys
    210                 215                 220

Lys Ala Ile Gly Gln Lys Ile Asp Asn Asn Asn Gly Leu Ala Ala Leu
225                 230                 235                 240

Asn Asn Gln Asn Gly Ser Leu Leu Ala Gly Ala Tyr Ala Ile Ser Thr
                245                 250                 255

Leu Ile Thr Glu Lys Leu Ser Lys Leu Lys Asn Leu Glu Glu Leu Lys
            260                 265                 270

Thr Glu Ile Ala Lys Ala Lys Lys Cys Ser Glu Glu Phe Thr Asn Lys
        275                 280                 285

Leu Lys Ser Gly His Ala Asp Leu Gly Lys Gln Asp Ala Thr Asp Asp
    290                 295                 300

His Ala Lys Ala Ala Ile Leu Lys Thr His Ala Thr Thr Asp Lys Gly
305                 310                 315                 320

Ala Lys Glu Phe Lys Asp Leu Phe Glu Ser Val Glu Gly Leu Leu Lys
                325                 330                 335

Ala Ala Gln Val Ala Leu Thr Asn Ser Val Lys Glu Leu Thr Ser Pro
            340                 345                 350

Val Val Ala Glu Ser Pro Lys Lys Pro
        355                 360


<210> SEQ ID NO 33
<211> LENGTH: 370
<212> TYPE: PRT
<213> ORGANISM: Borrelia sp.

<400> SEQUENCE: 33

Met Arg Gly Ser His His His His His His Ser Leu Thr Gly Lys Ala
1               5                   10                  15

Arg Leu Glu Ser Ser Val Lys Asp Ile Thr Asn Glu Ile Glu Lys Ala
            20                  25                  30
```

-continued

Ile Lys Glu Ala Glu Asp Ala Gly Val Lys Thr Asp Ala Phe Thr Glu
35 40 45

Thr Gln Thr Gly Gly Lys Val Ala Gly Pro Lys Ile Arg Ala Ala Lys
50 55 60

Ile Arg Val Ala Asp Leu Thr Ile Lys Phe Leu Glu Ala Thr Glu Glu
65 70 75 80

Glu Thr Ile Thr Phe Lys Glu Asn Gly Ala Gly Glu Asp Glu Phe Ser
85 90 95

Gly Ile Tyr Asp Leu Ile Leu Asn Ala Ala Lys Ala Val Glu Lys Ile
100 105 110

Gly Met Lys Asp Met Thr Lys Thr Val Glu Glu Ala Ala Lys Glu Asn
115 120 125

Pro Lys Thr Thr Ala Asn Gly Ile Ile Glu Ile Val Lys Val Met Lys
130 135 140

Ala Lys Val Glu Asn Ile Lys Glu Lys Gln Thr Lys Asn Gln Lys Lys
145 150 155 160

Lys Asn Thr Leu Ser Ala Ile Leu Met Thr Leu Phe Leu Phe Ile Ser
165 170 175

Cys Asn Asn Ser Gly Lys Gly Gly Asp Ser Ala Ser Thr Asn Pro Ala
180 185 190

Asp Glu Ser Ala Lys Gly Pro Asn Leu Thr Glu Ile Ser Lys Lys Ile
195 200 205

Thr Asp Ser Asn Ala Phe Val Leu Ala Val Lys Glu Val Glu Thr Leu
210 215 220

Val Leu Ser Ile Asp Glu Leu Ala Lys Lys Ala Ile Gly Gln Lys Ile
225 230 235 240

Asp Asn Asn Asn Gly Leu Ala Ala Leu Asn Asn Gln Asn Gly Ser Leu
245 250 255

Leu Ala Gly Ala Tyr Ala Ile Ser Thr Leu Ile Thr Glu Lys Leu Ser
260 265 270

Lys Leu Lys Asn Leu Glu Glu Leu Lys Thr Glu Ile Ala Lys Ala Lys
275 280 285

Lys Cys Ser Glu Glu Phe Thr Asn Lys Leu Lys Ser Gly His Ala Asp
290 295 300

Leu Gly Lys Gln Asp Ala Thr Asp Asp His Ala Lys Ala Ala Ile Leu
305 310 315 320

Lys Thr His Ala Thr Thr Asp Lys Gly Ala Lys Glu Phe Lys Asp Leu
325 330 335

Phe Glu Ser Val Glu Gly Leu Leu Lys Ala Ala Gln Val Ala Leu Thr
340 345 350

Asn Ser Val Lys Glu Leu Thr Ser Pro Val Val Ala Glu Ser Pro Lys
355 360 365

Lys Pro
370

<210> SEQ ID NO 34
<211> LENGTH: 350
<212> TYPE: PRT
<213> ORGANISM: Borrelia sp.

<400> SEQUENCE: 34

Met Thr Gly Ala Thr Lys Ile Arg Leu Glu Arg Ser Ala Lys Asp Ile
1 5 10 15

Thr Asp Glu Ile Asp Ala Ile Lys Lys Asp Ala Ala Leu Lys Gly Val
20 25 30

Asn Phe Asp Ala Phe Lys Asp Lys Lys Thr Gly Ser Gly Val Ser Glu
35 40 45

Asn Pro Phe Ile Leu Glu Ala Lys Val Arg Ala Thr Thr Val Ala Glu
50 55 60

Lys Phe Val Ile Ala Ile Glu Glu Glu Ala Thr Lys Leu Lys Glu Thr
65 70 75 80

Gly Ser Ser Gly Glu Phe Ser Ala Met Tyr Asp Leu Met Phe Glu Val
85 90 95

Ser Lys Pro Leu Gln Lys Leu Gly Ile Gln Glu Met Thr Lys Thr Val
100 105 110

Ser Asp Ala Ala Glu Glu Asn Pro Pro Thr Thr Ala Gln Gly Val Leu
115 120 125

Glu Ile Ala Lys Lys Met Arg Glu Lys Leu Gln Arg Val His Thr Lys
130 135 140

Asn Tyr Cys Thr Leu Lys Lys Lys Glu Asn Ser Thr Phe Thr Asp Glu
145 150 155 160

Lys Cys Lys Asn Asn Asn Thr Ser Ala Asn Ser Ala Asp Glu Ser Val
165 170 175

Lys Gly Pro Asn Leu Thr Glu Ile Ser Lys Lys Ile Thr Asp Ser Asn
180 185 190

Ala Val Leu Leu Ala Val Lys Glu Val Glu Ala Leu Leu Ser Ser Ile
195 200 205

Asp Glu Ile Ala Ala Lys Ala Ile Gly Lys Lys Ile His Gln Asn Asn
210 215 220

Gly Leu Asp Thr Glu Asn Asn His Asn Gly Ser Leu Leu Ala Gly Ala
225 230 235 240

Tyr Ala Ile Ser Thr Leu Ile Lys Gln Lys Leu Asp Gly Leu Lys Asn
245 250 255

Glu Gly Leu Lys Glu Lys Ile Asp Ala Ala Lys Lys Cys Ser Glu Thr
260 265 270

Phe Thr Asn Lys Leu Lys Glu Lys His Thr Asp Ser Phe Gly Lys Glu
275 280 285

Gly Val Thr Asp Ala Asp Ala Lys Glu Ala Ile Leu Lys Thr Asn Gly
290 295 300

Thr Lys Thr Lys Gly Ala Glu Glu Leu Gly Lys Leu Phe Glu Ser Val
305 310 315 320

Glu Val Leu Ser Lys Ala Ala Lys Glu Met Leu Ala Asn Ser Val Lys
325 330 335

Glu Leu Thr Ser Pro Val Val Ala Glu Ser Pro Lys Lys Pro
340 345 350

<210> SEQ ID NO 35
<211> LENGTH: 359
<212> TYPE: PRT
<213> ORGANISM: Borrelia sp.

<400> SEQUENCE: 35

Met Arg Gly Ser His His His His His His Thr Gly Ala Thr Lys Ile
1 5 10 15

Arg Leu Glu Arg Ser Ala Lys Asp Ile Thr Asp Glu Ile Asp Ala Ile
20 25 30

Lys Lys Asp Ala Ala Leu Lys Gly Val Asn Phe Asp Ala Phe Lys Asp
35 40 45

Lys Lys Thr Gly Ser Gly Val Ser Glu Asn Pro Phe Ile Leu Glu Ala

-continued

```
    50                  55                  60

Lys Val Arg Ala Thr Thr Val Ala Glu Lys Phe Val Ile Ala Ile Glu
65                  70                  75                  80

Glu Glu Ala Thr Lys Leu Lys Glu Thr Gly Ser Ser Gly Glu Phe Ser
                85                  90                  95

Ala Met Tyr Asp Leu Met Phe Glu Val Ser Lys Pro Leu Gln Lys Leu
            100                 105                 110

Gly Ile Gln Glu Met Thr Lys Thr Val Ser Asp Ala Ala Glu Glu Asn
        115                 120                 125

Pro Pro Thr Thr Ala Gln Gly Val Leu Glu Ile Ala Lys Lys Met Arg
    130                 135                 140

Glu Lys Leu Gln Arg Val His Thr Lys Asn Tyr Cys Thr Leu Lys Lys
145                 150                 155                 160

Lys Glu Asn Ser Thr Phe Thr Asp Glu Lys Cys Lys Asn Asn Asn Thr
                165                 170                 175

Ser Ala Asn Ser Ala Asp Glu Ser Val Lys Gly Pro Asn Leu Thr Glu
            180                 185                 190

Ile Ser Lys Lys Ile Thr Asp Ser Asn Ala Val Leu Leu Ala Val Lys
        195                 200                 205

Glu Val Glu Ala Leu Leu Ser Ser Ile Asp Glu Ile Ala Ala Lys Ala
    210                 215                 220

Ile Gly Lys Lys Ile His Gln Asn Asn Gly Leu Asp Thr Glu Asn Asn
225                 230                 235                 240

His Asn Gly Ser Leu Leu Ala Gly Ala Tyr Ala Ile Ser Thr Leu Ile
                245                 250                 255

Lys Gln Lys Leu Asp Gly Leu Lys Asn Glu Gly Leu Lys Glu Lys Ile
            260                 265                 270

Asp Ala Ala Lys Lys Cys Ser Glu Thr Phe Thr Asn Lys Leu Lys Glu
        275                 280                 285

Lys His Thr Asp Ser Phe Gly Lys Glu Gly Val Thr Asp Ala Asp Ala
    290                 295                 300

Lys Glu Ala Ile Leu Lys Thr Asn Gly Thr Lys Thr Lys Gly Ala Glu
305                 310                 315                 320

Glu Leu Gly Lys Leu Phe Glu Ser Val Glu Val Leu Ser Lys Ala Ala
                325                 330                 335

Lys Glu Met Leu Ala Asn Ser Val Lys Glu Leu Thr Ser Pro Val Val
            340                 345                 350

Ala Glu Ser Pro Lys Lys Pro
        355


<210> SEQ ID NO 36
<211> LENGTH: 493
<212> TYPE: PRT
<213> ORGANISM: Borrelia sp.

<400> SEQUENCE: 36

Met Thr Gly Glu Thr Lys Ile Arg Leu Glu Ser Ser Ala Gln Glu Ile
1               5                   10                  15

Lys Asp Glu Ile Asn Lys Ile Lys Ala Asn Ala Lys Lys Glu Gly Val
            20                  25                  30

Lys Phe Glu Ala Phe Thr Asp Lys Gln Thr Gly Ser Lys Val Ser Glu
        35                  40                  45

Lys Pro Glu Phe Ile Leu Lys Ala Lys Ile Lys Ala Ile Gln Val Ala
    50                  55                  60
```

-continued

```
Glu Lys Phe Val Lys Ala Ile Lys Glu Glu Ala Glu Lys Leu Lys Lys
65                  70                  75                  80

Ser Gly Ser Ser Gly Ala Phe Ser Ala Met Tyr Asp Leu Met Leu Asp
                85                  90                  95

Val Ser Lys Pro Leu Glu Glu Ile Gly Ile Gln Lys Met Thr Gly Thr
            100                 105                 110

Val Thr Lys Glu Ala Glu Lys Thr Pro Pro Thr Thr Ala Glu Gly Ile
        115                 120                 125

Leu Ala Ile Ala Gln Ala Met Glu Glu Lys Leu Asn Asn Val Asn Lys
    130                 135                 140

Lys Gln Gln Asp Ala Leu Lys Asn Leu Glu Glu Lys Ala Asn Thr Ala
145                 150                 155                 160

Ala Thr Thr Ser Gly Thr Gly Lys Ala Arg Leu Glu Ser Ser Val Lys
                165                 170                 175

Asp Ile Thr Asp Glu Ile Asp Lys Ala Ile Lys Glu Ala Ile Ala Asp
            180                 185                 190

Gly Val Lys Leu Asn Glu Leu Glu Glu Asn Lys Thr Gly Ala Lys Lys
        195                 200                 205

Gly Gly Pro Gln Ile Arg Asp Ala Lys Ile Arg Val Ile Asn Leu Ser
    210                 215                 220

Val Lys Phe Leu Lys Glu Ile Glu Glu Glu Ala Asn Ile Leu Lys Asp
225                 230                 235                 240

Asn Val Gly Met Asn Lys Val Asp Lys Asp Gln Leu Leu Lys Asp Met
                245                 250                 255

Tyr Asp Leu Met Leu Asn Ala Ala Gly Ser Leu Gln Lys Leu Gly Leu
            260                 265                 270

Gln Glu Met Ile Lys Thr Val Thr Gln Ala Ala Glu Lys Thr Pro Pro
        275                 280                 285

Thr Thr Val Glu Gly Ile Leu Met Ile Ala Asn Thr Ile Glu Asp Lys
    290                 295                 300

Leu Lys Lys Ile Lys Gly Lys Gln Glu Thr Asn Lys Lys Asp Glu Ser
305                 310                 315                 320

Ala Lys Gly Pro Asn Leu Thr Val Ile Ser Lys Lys Ile Thr Asp Ser
                325                 330                 335

Asn Ala Phe Leu Leu Ala Val Lys Glu Val Glu Ala Leu Leu Ser Ser
            340                 345                 350

Ile Asp Glu Leu Ser Lys Ala Ile Gly Lys Lys Ile Lys Asn Asp Gly
        355                 360                 365

Thr Leu Asp Asn Glu Ala Asn Arg Asn Glu Ser Leu Ile Ala Gly Ala
    370                 375                 380

Tyr Glu Ile Ser Lys Leu Ile Thr Gln Lys Leu Ser Val Leu Asn Ser
385                 390                 395                 400

Glu Glu Leu Lys Glu Lys Ile Lys Glu Ala Lys Asp Cys Ser Glu Lys
                405                 410                 415

Phe Thr Thr Lys Leu Lys Asp Ser His Ala Glu Leu Gly Ile Gln Ser
            420                 425                 430

Val Gln Asp Asp Asn Ala Lys Lys Ala Ile Leu Lys Thr His Gly Thr
        435                 440                 445

Lys Asp Lys Gly Ala Lys Glu Leu Glu Glu Leu Phe Lys Ser Leu Glu
    450                 455                 460

Ser Leu Ser Lys Ala Ala Gln Ala Ala Leu Thr Asn Ser Val Lys Glu
465                 470                 475                 480

Leu Thr Asn Pro Val Val Ala Glu Ser Pro Lys Lys Pro
```

485 490

<210> SEQ ID NO 37
<211> LENGTH: 502
<212> TYPE: PRT
<213> ORGANISM: Borrelia sp.

<400> SEQUENCE: 37

```
Met Arg Gly Ser His His His His His His Thr Gly Glu Thr Lys Ile
1               5                   10                  15

Arg Leu Glu Ser Ser Ala Gln Glu Ile Lys Asp Glu Ile Asn Lys Ile
            20                  25                  30

Lys Ala Asn Ala Lys Lys Glu Gly Val Lys Phe Glu Ala Phe Thr Asp
        35                  40                  45

Lys Gln Thr Gly Ser Lys Val Ser Glu Lys Pro Glu Phe Ile Leu Lys
    50                  55                  60

Ala Lys Ile Lys Ala Ile Gln Val Ala Glu Lys Phe Val Lys Ala Ile
65                  70                  75                  80

Lys Glu Glu Ala Glu Lys Leu Lys Lys Ser Gly Ser Ser Gly Ala Phe
                85                  90                  95

Ser Ala Met Tyr Asp Leu Met Leu Asp Val Ser Lys Pro Leu Glu Glu
            100                 105                 110

Ile Gly Ile Gln Lys Met Thr Gly Thr Val Thr Lys Glu Ala Glu Lys
        115                 120                 125

Thr Pro Pro Thr Thr Ala Glu Gly Ile Leu Ala Ile Ala Gln Ala Met
    130                 135                 140

Glu Glu Lys Leu Asn Asn Val Asn Lys Lys Gln Gln Asp Ala Leu Lys
145                 150                 155                 160

Asn Leu Glu Glu Lys Ala Asn Thr Ala Ala Thr Thr Ser Gly Thr Gly
                165                 170                 175

Lys Ala Arg Leu Glu Ser Ser Val Lys Asp Ile Thr Asp Glu Ile Asp
            180                 185                 190

Lys Ala Ile Lys Glu Ala Ile Ala Asp Gly Val Lys Leu Asn Glu Leu
        195                 200                 205

Glu Glu Asn Lys Thr Gly Ala Lys Lys Gly Gly Pro Gln Ile Arg Asp
    210                 215                 220

Ala Lys Ile Arg Val Ile Asn Leu Ser Val Lys Phe Leu Lys Glu Ile
225                 230                 235                 240

Glu Glu Glu Ala Asn Ile Leu Lys Asp Asn Val Gly Met Asn Lys Val
                245                 250                 255

Asp Lys Asp Gln Leu Leu Lys Asp Met Tyr Asp Leu Met Leu Asn Ala
            260                 265                 270

Ala Gly Ser Leu Gln Lys Leu Gly Leu Gln Glu Met Ile Lys Thr Val
        275                 280                 285

Thr Gln Ala Ala Glu Lys Thr Pro Pro Thr Thr Val Glu Gly Ile Leu
    290                 295                 300

Met Ile Ala Asn Thr Ile Glu Asp Lys Leu Lys Lys Ile Lys Gly Lys
305                 310                 315                 320

Gln Glu Thr Asn Lys Lys Asp Glu Ser Ala Lys Gly Pro Asn Leu Thr
                325                 330                 335

Val Ile Ser Lys Lys Ile Thr Asp Ser Asn Ala Phe Leu Leu Ala Val
            340                 345                 350

Lys Glu Val Glu Ala Leu Leu Ser Ser Ile Asp Glu Leu Ser Lys Ala
        355                 360                 365
```

```
Ile Gly Lys Lys Ile Lys Asn Asp Gly Thr Leu Asp Asn Glu Ala Asn
    370                 375                 380

Arg Asn Glu Ser Leu Ile Ala Gly Ala Tyr Glu Ile Ser Lys Leu Ile
385                 390                 395                 400

Thr Gln Lys Leu Ser Val Leu Asn Ser Glu Glu Leu Lys Glu Lys Ile
                405                 410                 415

Lys Glu Ala Lys Asp Cys Ser Glu Lys Phe Thr Thr Lys Leu Lys Asp
            420                 425                 430

Ser His Ala Glu Leu Gly Ile Gln Ser Val Gln Asp Asp Asn Ala Lys
        435                 440                 445

Lys Ala Ile Leu Lys Thr His Gly Thr Lys Asp Lys Gly Ala Lys Glu
    450                 455                 460

Leu Glu Glu Leu Phe Lys Ser Leu Glu Ser Leu Ser Lys Ala Ala Gln
465                 470                 475                 480

Ala Ala Leu Thr Asn Ser Val Lys Glu Leu Thr Asn Pro Val Val Ala
                485                 490                 495

Glu Ser Pro Lys Lys Pro
            500


<210> SEQ ID NO 38
<211> LENGTH: 506
<212> TYPE: PRT
<213> ORGANISM: Borrelia sp.

<400> SEQUENCE: 38

Met Arg Gly Ser His His His His His His Thr Gly Glu Thr Lys Ile
1               5                   10                  15

Arg Leu Glu Ser Ser Ala Gln Glu Ile Lys Asp Glu Ile Asn Lys Ile
            20                  25                  30

Lys Ala Asn Ala Lys Lys Glu Gly Val Lys Phe Glu Ala Phe Thr Asp
        35                  40                  45

Lys Gln Thr Gly Ser Lys Val Ser Glu Lys Pro Glu Phe Ile Leu Lys
    50                  55                  60

Ala Lys Ile Lys Ala Ile Gln Val Ala Glu Lys Phe Val Lys Ala Ile
65                  70                  75                  80

Lys Glu Glu Ala Glu Lys Leu Lys Lys Ser Gly Ser Ser Gly Ala Phe
                85                  90                  95

Ser Ala Met Tyr Asp Leu Met Leu Asp Val Ser Lys Pro Leu Glu Glu
            100                 105                 110

Ile Gly Ile Gln Lys Met Thr Gly Thr Val Thr Lys Glu Ala Glu Lys
        115                 120                 125

Thr Pro Pro Thr Thr Ala Glu Gly Ile Leu Ala Ile Ala Gln Ala Met
    130                 135                 140

Glu Glu Lys Leu Asn Asn Val Asn Lys Lys Gln Gln Asp Ala Leu Lys
145                 150                 155                 160

Asn Leu Glu Glu Lys Ala Asn Thr Ala Ala Thr Thr Ser Gly Thr Gly
                165                 170                 175

Lys Ala Arg Leu Glu Ser Ser Val Lys Asp Ile Thr Asp Glu Ile Asp
            180                 185                 190

Lys Ala Ile Lys Glu Ala Ile Ala Asp Gly Val Lys Leu Asn Glu Leu
        195                 200                 205

Glu Glu Asn Lys Thr Gly Ala Lys Lys Gly Gly Pro Gln Ile Arg Asp
    210                 215                 220

Ala Lys Ile Arg Val Ile Asn Leu Ser Val Lys Phe Leu Lys Glu Ile
225                 230                 235                 240
```

```
Glu Glu Glu Ala Asn Ile Leu Lys Asp Asn Val Gly Met Asn Lys Val
                245                 250                 255

Asp Lys Asp Gln Leu Leu Lys Asp Met Tyr Asp Leu Met Leu Asn Ala
            260                 265                 270

Ala Gly Ser Leu Gln Lys Leu Gly Leu Gln Glu Met Ile Lys Thr Val
        275                 280                 285

Thr Gln Ala Ala Glu Lys Thr Pro Pro Thr Thr Val Glu Gly Ile Leu
    290                 295                 300

Met Ile Ala Asn Thr Ile Glu Asp Lys Leu Lys Lys Ile Lys Gly Lys
305                 310                 315                 320

Gln Glu Thr Asn Lys Lys Gly Ser Gly Gly Asp Glu Ser Ala Lys Gly
                325                 330                 335

Pro Asn Leu Thr Val Ile Ser Lys Lys Ile Thr Asp Ser Asn Ala Phe
            340                 345                 350

Leu Leu Ala Val Lys Glu Val Glu Ala Leu Leu Ser Ser Ile Asp Glu
        355                 360                 365

Leu Ser Lys Ala Ile Gly Lys Lys Ile Lys Asn Asp Gly Thr Leu Asp
    370                 375                 380

Asn Glu Ala Asn Arg Asn Glu Ser Leu Ile Ala Gly Ala Tyr Glu Ile
385                 390                 395                 400

Ser Lys Leu Ile Thr Gln Lys Leu Ser Val Leu Asn Ser Glu Glu Leu
                405                 410                 415

Lys Glu Lys Ile Lys Glu Ala Lys Asp Cys Ser Glu Lys Phe Thr Thr
            420                 425                 430

Lys Leu Lys Asp Ser His Ala Glu Leu Gly Ile Gln Ser Val Gln Asp
        435                 440                 445

Asp Asn Ala Lys Lys Ala Ile Leu Lys Thr His Gly Thr Lys Asp Lys
    450                 455                 460

Gly Ala Lys Glu Leu Glu Glu Leu Phe Lys Ser Leu Glu Ser Leu Ser
465                 470                 475                 480

Lys Ala Ala Gln Ala Ala Leu Thr Asn Ser Val Lys Glu Leu Thr Asn
                485                 490                 495

Pro Val Val Ala Glu Ser Pro Lys Lys Pro
            500                 505
```

<210> SEQ ID NO 39
<211> LENGTH: 1086
<212> TYPE: DNA
<213> ORGANISM: Borrelia sp.

<400> SEQUENCE: 39

```
atgagcctga ccggcaaagc gcgtctggaa agcagcgtga aagatattac caacgaaatt      60

gaaaaagcga ttaaagaagc ggaagatgcg ggcgtgaaaa ccgatgcgtt taccgaaacc     120

cagaccggcg gcaaagtggc gggcccgaaa attcgtgcgg cgaaaattcg tgtggcggat     180

ctgaccatta aatttctgga agcgaccgaa gaagaaacca ttacctttaa agaaaatggc     240

gcgggcgaag atgaatttag cggcatttat gatctgattc tgaacgcggc gaaagcggtg     300

gaaaaaattg gcatgaaaga tatgaccaaa accgtggaag aagcggcgaa agaaaatccg     360

aaaaccaccg cgaacggtat tattgaaatt gtgaaagtga tgaaagcgaa agtggaaaat     420

attaaagaaa aacagaccaa aaaccagaaa aaaaaaaaca ccctgagcgc gattctgatg     480

accctgtttc tgtttattag ctgcaacaac agcggcaaag gcggcgatag cgcgagcacc     540

aacccggcgg atgaaagcgc gaaaggcccg aacctgaccg aaattagcaa aaaaatcacc     600
```

-continued gatagcaacg cgtttgtgct ggcggtgaaa gaagtggaaa ccctggttct gagcattgat 660
gaactggcga aaaaagcgat tggccagaaa atcgataaca acaacggcct ggcggcgctg 720
aacaaccaga acggcagcct gctggcgggt gcgtatgcga ttagcaccct gattaccgaa 780
aaactgagca aactgaaaaa cctggaagaa ctgaaaaccg aaatcgcgaa agcgaaaaaa 840
tgcagcgaag aatttaccaa caaactgaaa agcggccatg cggatctggg caaacaggat 900
gcgaccgatg atcatgcgaa agcggcgatt ctgaaaaccc atgcgaccac cgataaaggc 960
gcgaaagaat ttaaagacct gttcgaaagc gtggaaggcc tgctgaaagc ggcgcaggtg 1020
gcgctgacca acagcgtgaa agaactgacc agcccggtgg ttgcggaaag cccgaaaaaa 1080
ccgtaa 1086

<210> SEQ ID NO 40
<211> LENGTH: 1113
<212> TYPE: DNA
<213> ORGANISM: Borrelia sp.

<400> SEQUENCE: 40
atgaggggat cccatcatca tcatcatcat agcctgaccg gcaaagcgcg tctggaaagc 60
agcgtgaaag atattaccaa cgaaattgaa aaagcgatta aagaagcgga agatgcgggc 120
gtgaaaaccg atgcgtttac cgaaacccag accggcggca aagtggcggg cccgaaaatt 180
cgtgcggcga aaattcgtgt ggcggatctg accattaaat ttctggaagc gaccgaagaa 240
gaaaccatta cctttaaaga aaatggcgcg ggcgaagatg aatttagcgg catttatgat 300
ctgattctga acgcggcgaa agcggtggaa aaaattggca tgaaagatat gaccaaaacc 360
gtggaagaag cggcgaaaga aaatccgaaa accaccgcga acggtattat tgaaattgtg 420
aaagtgatga aagcgaaagt ggaaaatatt aaagaaaaac agaccaaaaa ccagaaaaaa 480
aaaaacaccc tgagcgcgat tctgatgacc ctgtttctgt ttattagctg caacaacagc 540
ggcaaaggcg gcgatagcgc gagcaccaac ccggcggatg aaagcgcgaa aggcccgaac 600
ctgaccgaaa ttagcaaaaa aatcaccgat agcaacgcgt ttgtgctggc ggtgaaagaa 660
gtggaaaccc tggttctgag cattgatgaa ctggcgaaaa aagcgattgg ccagaaaatc 720
gataacaaca acggcctggc ggcgctgaac aaccagaacg gcagcctgct ggcgggtgcg 780
tatgcgatta gcaccctgat taccgaaaaa ctgagcaaac tgaaaaacct ggaagaactg 840
aaaaccgaaa tcgcgaaagc gaaaaaatgc agcgaagaat ttaccaacaa actgaaaagc 900
ggccatgcgg atctgggcaa acaggatgcg accgatgatc atgcgaaagc ggcgattctg 960
aaaacccatg cgaccaccga taaaggcgcg aaagaattta aagacctgtt cgaaagcgtg 1020
gaaggcctgc tgaaagcggc gcaggtggcg ctgaccaaca gcgtgaaaga actgaccagc 1080
ccggtggttg cggaaagccc gaaaaaaccg taa 1113

<210> SEQ ID NO 41
<211> LENGTH: 1053
<212> TYPE: DNA
<213> ORGANISM: Borrelia sp.

<400> SEQUENCE: 41
atgaccggcg cgaccaaaat ccgcctggaa cgcagcgcga aagatatcac agatgaaatc 60
gatgcgatca agaaagacgc ggcgctgaaa ggcgtcaact ttgatgcatt taaagataaa 120
aagaccgggt ctggagttag cgagaatcca tttattctgg aagcgaaagt tcgtgctacg 180

-continued

```
acggtggcag aaaaatttgt gattgcgatt gaagaagaag caacgaaact gaaagaaacc    240

ggcagcagtg gcgaatttag tgcgatgtat gacctgatgt ttgaggtctc taaaccgctg    300

cagaaactgg ggattcaaga aatgaccaag acggtatctg atgcagcgga agaaaacccg    360

cctacgacgg cgcaaggcgt cctggaaatt gccaagaaaa tgcgcgaaaa actgcaacgc    420

gttcatacca aaaattattg cactctgaag aagaaagaga atagcacttt tacggatgaa    480

aaatgtaaaa ataataacac cagcgcgaac agcgcggatg aaagcgtgaa aggcccgaac    540

ctgaccgaaa ttagcaaaaa aatcaccgat agcaacgcgg tgctgctggc ggtgaaagaa    600

gtggaagcgc tgctgagcag cattgatgaa attgcggcga aagcgattgg caaaaaaatc    660

catcagaaca acggcctgga taccgaaaac aaccataacg gcagcctgct ggcgggtgcg    720

tatgcgatta gcaccctgat taaacagaaa ctggatggcc tgaaaaacga aggcttaaaa    780

gaaaaaattg atgcggcgaa aaaatgcagc gaaaccttca ccaacaaact gaaagaaaaa    840

cataccgata gcttcggtaa agaaggcgtg accgacgcgg atgcgaaaga agcgattctg    900

aaaaccaacg gcaccaaaac caaaggcgcg gaagaactgg gcaaactgtt tgaaagcgtg    960

gaagttctga gcaaagcggc caaagaaatg ctggcgaaca gcgtgaaaga actgaccagc   1020

ccggtggtgg cagaatctcc gaaaaagccc taa                                 1053
```

<210> SEQ ID NO 42
<211> LENGTH: 1080
<212> TYPE: DNA
<213> ORGANISM: Borrelia sp.

<400> SEQUENCE: 42

```
atgaggggat cccatcatca tcatcatcac accggcgcga ccaaaatccg cctggaacgc     60

agcgcgaaag atatcacaga tgaaatcgat gcgatcaaga aagacgcggc gctgaaaggc    120

gtcaactttg atgcatttaa agataaaaag accgggtctg gagttagcga gaatccattt    180

attctggaag cgaaagttcg tgctacgacg gtggcagaaa aatttgtgat tgcgattgaa    240

gaagaagcaa cgaaactgaa agaaaccggc agcagtggcg aatttagtgc gatgtatgac    300

ctgatgtttg aggtctctaa accgctgcag aaactgggga ttcaagaaat gaccaagacg    360

gtatctgatg cagcggaaga aaacccgcct acgacggcgc aaggcgtcct ggaaattgcc    420

aagaaaatgc gcgaaaaact gcaacgcgtt cataccaaaa attattgcac tctgaagaag    480

aaagagaata gcacttttac ggatgaaaaa tgtaaaaata ataacaccag cgcgaacagc    540

gcggatgaaa gcgtgaaagg cccgaacctg accgaaatta gcaaaaaaat caccgatagc    600

aacgcggtgc tgctggcggt gaaagaagtg gaagcgctgc tgagcagcat tgatgaaatt    660

gcggcgaaag cgattggcaa aaaaatccat cagaacaacg gcctggatac cgaaaacaac    720

cataacggca gcctgctggc gggtgcgtat gcgattagca ccctgattaa acagaaactg    780

gatggcctga aaaacgaagg cttaaaagaa aaaattgatg cggcgaaaaa atgcagcgaa    840

accttcacca acaaactgaa agaaaaacat accgatagct tcggtaaaga aggcgtgacc    900

gacgcggatg cgaaagaagc gattctgaaa accaacggca ccaaaaccaa aggcgcggaa    960

gaactgggca aactgtttga aagcgtggaa gttctgagca aagcggccaa agaaatgctg   1020

gcgaacagcg tgaaagaact gaccagcccg gtggtggcag aatctccgaa aaagccctaa   1080
```

<210> SEQ ID NO 43
<211> LENGTH: 1482
<212> TYPE: DNA
<213> ORGANISM: Borrelia sp.

<400> SEQUENCE: 43
atgactggtg aaacgaaaat tcgtctggaa tcatccgctc aggagattaa agacgaaatc 60
aacaaaatta aagcaaacgc caagaaagaa ggcgtgaagt ttgaagcgtt taccgataaa 120
cagaccggca gcaaagtttc agaaaaaccg gagtttattc tgaaagccaa aattaaagcg 180
atccaggttg cggaaaaatt cgtgaaagcg attaaagaag aagccgaaaa actgaaaaaa 240
tctggttcga gcggcgcatt ttccgcaatg tatgatctga tgctggatgt aagcaaaccg 300
ctggaagaga ttggcattca gaaaatgacc ggcactgtca caaaggaagc ggaaaaaaca 360
ccgccaacca ctgcagaagg gattctggcg atcgcccagg cgatggaaga gaaactgaac 420
aacgttaata aaaaacagca ggatgcactg aaaaacctgg aagagaaggc gaacaccgcg 480
gcgactacgt cagggaccgg taaagcgcgt ctggaaagct cggtaaaaga tatcacagac 540
gaaattgaca aagccatcaa agaagccatt gcagacggcg ttaaactgaa tgaactggaa 600
gaaaataaaa ccggtgcgaa aaaaggtggc ccgcagattc gcgatgcgaa aatccgtgtg 660
atcaacctga gcgttaaatt cctgaaagaa atcgaggagg aagcaaacat cctgaaggat 720
aatgttggca tgaacaaggt agataaagat cagctgctga aagacatgta cgacctgatg 780
ctgaacgcgg ctggcagtct gcagaaactg ggtctgcagg aaatgatcaa aacggttacc 840
caagctgcgg aaaaaacccc accgaccacg gttgaaggca ttctgatgat tgcaaacacc 900
attgaagaca aactgaagaa aatcaaaggc aaacaggaaa caaacaaaaa agatgaaagc 960
gcaaaaggcc cgaatctgac cgtcatttct aagaaaatta ccgattcaaa cgcgtttctg 1020
ctggccgtga aagaggttga agccctgctg tcctcgattg atgaactgag caaagctatc 1080
ggaaagaaaa ttaaaaatga tgggacgctg gataacgagg caaatcgcaa tgaaagcctg 1140
attgcaggcg catatgaaat cagtaaactg attacacaga aactgagtgt cctgaacagc 1200
gaagaactga aagaaaaaat caaagaagcc aaagactgtt cggaaaagtt tactaccaaa 1260
ctgaaagact cgcatgctga actgggtatt cagtcagtgc aagatgataa tgcgaaaaaa 1320
gcaattctga aacgcacgg gacgaaagat aaaggtgcca aagagctgga agaactgttt 1380
aaaagcctgg aatcgctgag taaagccgca caggccgcgc tgaccaatag cgtgaaggaa 1440
ctgactaatc cggttgtagc agaatctccg aaaaagccgt aa 1482

<210> SEQ ID NO 44
<211> LENGTH: 1509
<212> TYPE: DNA
<213> ORGANISM: Borrelia sp.

<400> SEQUENCE: 44
atgaggggat cccatcatca ccaccatcat actggtgaaa cgaaaattcg tctggaatca 60
tccgctcagg agattaaaga cgaaatcaac aaaattaaag caaacgccaa gaaagaaggc 120
gtgaagtttg aagcgtttac cgataaacag accggcagca aagtttcaga aaaaccggag 180
tttattctga aagccaaaat taaagcgatc caggttgcgg aaaaattcgt gaaagcgatt 240
aaagaagaag ccgaaaaact gaaaaaatct ggttcgagcg gcgcattttc cgcaatgtat 300
gatctgatgc tggatgtaag caaaccgctg gaagagattg gcattcagaa aatgaccggc 360
actgtcacaa aggaagcgga aaaaacaccg ccaaccactg cagaagggat tctggcgatc 420
gcccaggcga tggaagagaa actgaacaac gttaataaaa aacagcagga tgcactgaaa 480
aacctggaag agaaggcgaa caccgcggcg actacgtcag ggaccggtaa agcgcgtctg 540

```
gaaagctcgg taaaagatat cacagacgaa attgacaaag ccatcaaaga agccattgca     600
gacggcgtta aactgaatga actggaagaa aataaaaccg gtgcgaaaaa aggtggcccg     660
cagattcgcg atgcgaaaat ccgtgtgatc aacctgagcg ttaaattcct gaaagaaatc     720
gaggaggaag caaacatcct gaaggataat gttggcatga acaaggtaga taaagatcag     780
ctgctgaaag acatgtacga cctgatgctg aacgcggctg gcagtctgca gaaactgggt     840
ctgcaggaaa tgatcaaaac ggttacccaa gctgcggaaa aaaccccacc gaccacggtt     900
gaaggcattc tgatgattgc aaacaccatt gaagacaaac tgaagaaaat caaaggcaaa     960
caggaaacaa acaaaaaaga tgaaagcgca aaaggcccga atctgaccgt catttctaag    1020
aaaattaccg attcaaacgc gtttctgctg gccgtgaaag aggttgaagc cctgctgtcc    1080
tcgattgatg aactgagcaa agctatcgga aagaaaatta aaaatgatgg gacgctggat    1140
aacgaggcaa atcgcaatga aagcctgatt gcaggcgcat atgaaatcag taaactgatt    1200
acacagaaac tgagtgtcct gaacagcgaa gaactgaaag aaaaaatcaa agaagccaaa    1260
gactgttcgg aaaagtttac taccaaactg aaagactcgc atgctgaact gggtattcag    1320
tcagtgcaag atgataatgc gaaaaaagca attctgaaaa cgcacgggac gaaagataaa    1380
ggtgccaaag agctggaaga actgtttaaa agcctggaat cgctgagtaa agccgcacag    1440
gccgcgctga ccaatagcgt gaaggaactg actaatccgg ttgtagcaga atctccgaaa    1500
aagccgtaa                                                            1509
```

```
<210> SEQ ID NO 45
<211> LENGTH: 1521
<212> TYPE: DNA
<213> ORGANISM: Borrelia sp.

<400> SEQUENCE: 45

atgaggggat cccatcatca ccaccatcat actggtgaaa cgaaaattcg tctggaatca      60
tccgctcagg agattaaaga cgaaatcaac aaaattaaag caaacgccaa gaaagaaggc     120
gtgaagtttg aagcgtttac cgataaacag accggcagca aagtttcaga aaaaccggag     180
tttattctga aagccaaaat taaagcgatc caggttgcgg aaaaattcgt gaaagcgatt     240
aaagaagaag ccgaaaaact gaaaaaatct ggttcgagcg gcgcattttc cgcaatgtat     300
gatctgatgc tggatgtaag caaaccgctg gaagagattg gcattcagaa aatgaccggc     360
actgtcacaa aggaagcgga aaaaacaccg ccaaccactg cagaagggat tctggcgatc     420
gcccaggcga tggaagagaa actgaacaac gttaataaaa aacagcagga tgcactgaaa     480
aacctggaag agaaggcgaa caccgcggcg actacgtcag ggaccggtaa agcgcgtctg     540
gaaagctcgg taaaagatat cacagacgaa attgacaaag ccatcaaaga agccattgca     600
gacggcgtta aactgaatga actggaagaa aataaaaccg gtgcgaaaaa aggtggcccg     660
cagattcgcg atgcgaaaat ccgtgtgatc aacctgagcg ttaaattcct gaaagaaatc     720
gaggaggaag caaacatcct gaaggataat gttggcatga acaaggtaga taaagatcag     780
ctgctgaaag acatgtacga cctgatgctg aacgcggctg gcagtctgca gaaactgggt     840
ctgcaggaaa tgatcaaaac ggttacccaa gctgcggaaa aaaccccacc gaccacggtt     900
gaaggcattc tgatgattgc aaacaccatt gaagacaaac tgaagaaaat caaaggcaaa     960
caggaaacaa acaaaaaagg ttccgggggt gatgaaagcg caaaaggccc gaatctgacc    1020
gtcatttcta agaaaattac cgattcaaac gcgtttctgc tggccgtgaa agaggttgaa    1080
gccctgctgt cctcgattga tgaactgagc aaagctatcg gaaagaaaat taaaaatgat    1140
```

-continued

```
gggacgctgg ataacgaggc aaatcgcaat gaaagcctga ttgcaggcgc atatgaaatc   1200

agtaaactga ttacacagaa actgagtgtc ctgaacagcg aagaactgaa agaaaaaatc   1260

aaagaagcca aagactgttc ggaaaagttt actaccaaac tgaaagactc gcatgctgaa   1320

ctgggtattc agtcagtgca agatgataat gcgaaaaaag caattctgaa aacgcacggg   1380

acgaaagata aaggtgccaa agagctggaa gaactgttta aaagcctgga atcgctgagt   1440

aaagccgcac aggccgcgct gaccaatagc gtgaaggaac tgactaatcc ggttgtagca   1500

gaatctccga aaaagccgta a                                             1521


<210> SEQ ID NO 46
<211> LENGTH: 4
<212> TYPE: PRT
<213> ORGANISM: Artificial Sequence
<220> FEATURE:
<223> OTHER INFORMATION: Synthetic Construct - aa+ 2

<400> SEQUENCE: 46

Gly Ser Gly Gly
1


<210> SEQ ID NO 47
<211> LENGTH: 12
<212> TYPE: DNA
<213> ORGANISM: Artificial Sequence
<220> FEATURE:
<223> OTHER INFORMATION: Synthetic Construct - DNA aa+ 2

<400> SEQUENCE: 47

ggttccgggg gt                                                          12
```

PROTEINS USED FOR THE DIAGNOSIS OF LYME BORRELIOSIS

This is a Division of application Ser. No. 13/388,168 filed Jan. 31, 2012, now U.S. Pat. No. 8,895,257, which in turn is a National Phase entry of PCT/FR2010/051787 filed Aug. 27, 2010, which claims priority to FR 0904094 filed Aug. 28, 2009. The disclosure of the prior applications is hereby incorporated by reference herein in its entirety.

Lyme borreliosis (LB) is a noncontagious infectious disease caused by a spirochete called *Borrelia burgdorferi*, which is transmitted to humans via a bite by a tick of the genus *Ixodes*. Without treatment, LB leads to various pathological disorders (dermatological, arthritic, cardiac, neurological and sometimes ocular disorders). It is the most common vector-borne disease in the USA and in certain temperate countries of the northern hemisphere.

Several *borrelia* species, currently denoted under the group term *burgdorferi* or *Borrelia burgdorferi* sensu lato (including *Borrelia burgdorferi* sensu stricto, *B. garinii* and *B. afzelii*), are involved in this infection. These species are pathogenic to humans.

In the United States, the infectious species involved is *Borrelia burgdorferi* sensu stricto. In Europe, in addition to this species, *B. garinii* and *B. afzelii* are involved. In Asia, the species involved are *B. garinii* and *B. afzelii.*

In the United States, approximately 10 000 cases are reported. In Europe, the incidence rates vary from less than 5 per 100 000.

Lyme borreliosis progresses by passing through three distinct phases, from early infection to the late phase. The early stage (stage I) may be asymptomatic or reflected by flu-like symptoms. In 50-80% of cases, the appearance of an inflammatory skin rash with a very particular appearance, called erythema migrans (EM) is noted several days after the bite by the tick. In the absence of treatment, the dissemination of the *Borrelia* via the blood is reflected a few weeks later by the occurrence of inflammatory arthritis, neurological (neuroborreliosis) and meningeal involvement, and skin and cardiac manifestations (stage II). After several months or years, the disease progresses to a chronic atrophicans form, encephalopathy, encephalomyelitis and chronic arthritis (stage III).

A particular organotropism exists for each of the species of *Borrelia burgdorferi*. While the first stage of erythema migrans is without distinction linked to the three species, the progression to a neurological form is preferentially associated with the species *B. garinii*, arthritis is more associated with *B. burgdorferi* sensu stricto, and acrodermatitis chronica atrophicans is specific for *B. afzelii.*

The similarity of the clinical symptoms between Lyme borreliosis and other unrelated diseases, and also the variability in manifestations, makes clinical diagnosis difficult. The diagnosis of borreliosis can be particularly difficult on the basis of clinical observations, if case history evidence is absent (tick bite or EM). The early stage of the disease may be without visible symptoms up to the time it reaches very advanced clinical stages.

Consequently, the diagnosis of LB is based on clinical signs but also on the detection of pathogenic *Borrelia burgdorferi*-specific antibodies in the serum, most commonly by ELISA (Enzyme Linked ImmunoSorbent Assay) or else EIA or IFA.

In Europe, the evaluation of the serological response is complicated owing to the existence of three pathogenic species and to the interspecies variability for the major immunodominant antigens. The antigens currently routinely used for detecting LB IgGs and IgMs are ultrasound-treated cell samples of *Borrelia burgdorferi* sensu lato. The performance levels of the serological assays with these antigens, in terms of specificity and sensitivity, are highly variable. Thus, owing to insufficient specificity, involving cross reactivities with antibodies associated with pathogenic bacteria, in particular *Treponema pallidum* (etiological agent for syphilis), spirochetes, rickettsiae, ehrlichia, or *Helicobacter pylori*, the diagnosis of samples having tested positive by ELISA must be confirmed by immunoblotting. Sensitivity is also a major factor. This is because *Borrelia burgdorferi* sensu lato expresses various surface proteins via adaptation to various microenvironments, such that the genetic diversity and the differential expression of the *Borrelia burgdorferi* genes in patients have important implications for the development of serological tests for LB.

It was therefore necessary to develop a kit which overcomes the abovementioned drawbacks and which more particularly meets the expected specificity and sensitivity criteria.

The VlsE protein (surface expressed lipoprotein with Extensive antigenic Variation) is mainly expressed, in vivo, transiently and rapidly after infection of the host. It is very immunogenic in the infected host, involving the production of IgGs and IgMs. The Vls locus is located on a linear plasmid of 28 kb (Ip28-1) present in the three *Borrelia* genospecies responsible for Lyme disease and composed of silent cassettes and an expression site (VlsE). In vivo, random recombinations between expression cassettes and silent cassettes occur during infection and are responsible for the antigenic variability of VlsE. The VlsE protein is composed of six variable regions VR1-VR6, located at the surface of the VlsE protein, spaced out by "invariable" regions IR1-IR6.

It is known that the VlsE proteins exhibit considerable interspecies and intraspecies heterogeneity. In 2004, Göttner et al. [1] described an identity of approximately 47 to 58% at the protein level of VlsE originating from four strains.

In order to overcome the abovementioned sensitivity and specificity problems, the inventors have produced a *Borrelia* chimeric protein comprising at least one sequence of the extracellular domain of a VlsE protein of a first *Borrelia* species corresponding to a predetermined strain and at least one sequence of an IR6 region of a VlsE protein of a second *Borrelia* species or of the first *Borrelia* species but corresponding to a strain different than that of the first species, said chimeric protein comprising (or consisting essentially of or else consisting of):

the sequence of the extracellular domain of the VlsE protein of the first *Borrelia* species which is composed of five variable regions VR1, VR2, VR3, VR4 and VR5 and of six invariable regions IR1, IR2, IR3, IR4, IR5 and IR6, said at least one sequence of the extracellular domain being selected from the group consisting of SEQ ID NOs: 1, 2, 3, 4 and 5 or a variant of one of said sequences SEQ ID NOs 1, 2, 3, 4 and 5, said variant exhibiting at least 50% identity (preferably at least 60% or at least 70% identity and advantageously at least 80% or at least 85% identity) with SEQ ID NOs 1, 2, 3, 4 and 5, respectively, on the condition that said variant is capable of forming an immunological complex with antibodies produced following a *Borrelia* infection, and the at least one sequence of the IR6 region of the second *Borrelia* species, or of the first *Borrelia* species but corresponding to a strain different than that of the first species, which is selected from the group consisting of SEQ ID NOs: 6, 7 and 8 or a variant of one of said sequences SEQ ID NOs 6, 7 and 8, said variant exhibiting at least 80% identity (preferably at least 85% and advantageously at least 90% identity) with SEQ ID NOs 6, 7 and 8, respectively, on the condition that the variant of said sequence is capable of forming an immunological complex with the antibodies produced following a *Borrelia* infection.

The chimeric protein identified above can in addition comprise a variable sequence VR6 of a *Borrelia* species, this sequence being identified in SEQ ID NO: 9 in the sequence listing.

A preferred chimera protein comprises (or consists essentially of or consists of):

- the sequence SEQ ID NO: 1 or a variant of said sequence SEQ ID NO: 1, said variant exhibiting at least 50% identity (preferably at least 60% or at least 70% identity and advantageously at least 80% or at least 85% identity) with SEQ ID NO: 1,
- the sequence SEQ ID NO: 6 or a variant of said sequence SEQ ID NO: 6, said variant exhibiting at least 80% identity (preferably at least 85% and advantageously at least 90% identity) with SEQ ID NO: 6,
- the sequence SEQ ID NO: 7 or a variant of said sequence SEQ ID NO: 7, said variant exhibiting at least 80% identity (preferably at least 85% and advantageously at least 90% identity) with SEQ ID NO: 7, and
- the sequence SEQ ID NO: 8 or a variant of said sequence SEQ ID NO: 8, said variant exhibiting at least 80% identity (preferably at least 85% and advantageously at least 90% identity) with SEQ ID NO: 8,
- and, optionally, the variable sequence VR6 identified in SEQ ID NO: 9.

Thus, one of the chimeric proteins of the invention comprises (or consists essentially of or consists of) the sequence SEQ ID NO: 1, the sequence SEQ ID NO: 6, the sequence SEQ ID NO: 7 and the sequence SEQ ID NO: 8, or even in addition the sequence SEQ ID NO: 9.

The preferred chimeric proteins of the invention are particularly identified as comprising (or consisting essentially of or consisting of) a sequence selected from SEQ ID NO: 20, SEQ ID NO: 21 and SEQ ID NO: 23; the most preferred protein being that which comprises or which consists of a sequence identified in SEQ ID NO: 20 in the sequence listing.

SEQ ID NO: 1 corresponds to the sequence of the VlsE extracellular domain of *B. garinii* (strain pBi) deleted of its signal sequence (aa 1-19) and of the C-terminal region of the mature protein located after the IR6 domain, i.e. this extracellular domain is composed of the IR1, VR1, IR2, VR2, IR3, VR3, IR4, VR4, IR5, VR5 and IR6 regions of *B. garinii* (strain pBi).

SEQ ID NO: 2 corresponds to the sequence of the VlsE extracellular domain of *B. garinii* (strain pBr) deleted of its signal sequence and of the C-terminal region of the mature protein located after the IR6 domain, i.e. this extracellular domain is composed of the IR1, VR1, IR2, VR2, IR3, VR3, IR4, VR4, IR5, VR5 and IR6 regions of *B. garinii* (strain pBr).

SEQ ID NO: 3 corresponds to the sequence of the VlsE extracellular domain of *B. garinii* (strain pLi) deleted of its signal sequence and of the C-terminal region of the mature protein located after the IR6 domain, i.e. this extracellular domain is composed of the IR1, VR1, IR2, VR2, IR3, VR3, IR4, VR4, IR5, VR5 and IR6 regions of *B. garinii* (strain pLi).

SEQ ID NO: 4 corresponds to the sequence of the VlsE extracellular domain of *B. afzelii* (strain pKo) deleted of its signal sequence and of the C-terminal region of the mature protein located after the IR6 domain, i.e. this extracellular domain is composed of the IR1, VR1, IR2, VR2, IR3, VR3, IR4, VR4, IR5, VR5 and IR6 regions of *B. afzelii* (strain pKo).

SEQ ID NO: 5 corresponds to the sequence of the VlsE extracellular domain of *B. burgdorferi* sensu stricto (strain B31) deleted of its signal sequence and of the C-terminal region of the mature protein located after the IR6 domain, i.e. this extracellular domain is composed of the IR1, VR1, IR2, VR2, IR3, VR3, IR4, VR4, IR5, VR5 and IR6 regions of *B. burgdorferi* sensu stricto (strain B31).

SEQ ID NO: 6 corresponds to the sequence of the IR6 domain of *B. burgdorferi* sensu stricto (strain B31).

SEQ ID NO: 7 corresponds to the sequence of the IR6 domain of *B. afzelii* (strain ACA-1).

SEQ ID NO: 8 corresponds to the sequence of the IR6 domain of *B. garinii* (strain Ip90).

SEQ ID NO: 9 corresponds to the sequence of the VR6 variable region of *B. burgdorferi* sensu stricto (strain B31). This sequence can be introduced into the construct as a spacer arm between the IR6 domains.

It is possible to add a sequence of at least 6 histidines (polyhistidine tail), identified in SEQ ID NO: 10, encoded by any one of the nucleic sequences identified in SEQ ID NOs 11, 12 and 13, at the N-terminal or C-terminal end of the protein in order to allow its purification on metal-chelate resin, and also additional amino acids represented in SEQ ID NO: 14 and encoded by the sequence SEQ ID NO: 15, upstream of the polyhistidine tail. In this configuration, the protein comprises or consists of a sequence identified as SEQ ID NO: 21. Alternatively, it is possible to place a sequence of 8 histidines, represented in SEQ ID NO: 16 and encoded by SEQ ID NO: 17, in the N-terminal position of the protein in place of the 6-histidine sequence, which makes it possible to stabilize the attachment of the recombinant protein to the metal-chelate resin and to improve the purification conditions, and also additional amino acids represented in SEQ ID NO: 18 and encoded by the sequence SEQ ID NO: 19. In this configuration, the protein comprises or consists of a sequence identified as SEQ ID NO: 23.

The preferred proteins of the invention are those identified as SEQ ID NOs: 21 and 23, respectively encoded by the sequences SEQ ID NOs: 22 and 24.

The subject of the invention is also the DNA sequences encoding the proteins as defined above, and in particular the sequences identified as SEQ ID NOs: 22 and 24.

The subject of the invention is also an expression cassette which is functional in a cell derived from a prokaryotic organism (example: *Escherichia coli*) or a eukaryotic organism, such as a yeast (example: *Pichia, Schizosaccharomyces*), allowing the expression of the nucleic acid described above (DNA), when it is placed under the control of the elements allowing its expression, and also the vector comprising such a cassette.

The protein of the invention can in particular be used for the diagnosis of a *Borrelia* infection. Thus, the subject of the present invention is a method for the in vitro diagnosis of Lyme borreliosis in a biological sample (for example a serum, blood, plasma, etc., sample), according to which the biological sample is brought into contact with at least one protein as defined above and it is determined whether there is formation of an immunological complex between said protein and antibodies of the biological sample (IgGs and/or IgMs), for example by adding at least one anti-human-immunoglobulin labeled with any appropriate label. The term "label" is intended to mean a tracer capable of generating a signal. A nonlimiting list of these tracers comprises enzymes which produce a signal detectable, for example, by colorimetry, fluorescence or luminescence, for instance horseradish peroxidase, alkaline phosphatase, β-galactosidase or glucose-6-phosphate dehydrogenase; chromophores, for instance fluorescent, luminescent or coloring compounds; electron dense groups that can be detected by electron microscopy or via their electrical properties, for instance conductivity, by amperometry or voltammetry methods, or by impedance measurements; groups that can be detected by optical methods, for instance diffraction, surface plasmon resonance or contact angle variation, or by physical methods, for instance atomic force spectroscopy, tunnel effect, etc.; radioactive molecules, for instance $^{32}P$, $^{35}S$ or $^{125}I$. Preferably, the protein is immobilized on a solid support which may be the tip of a Vidas® apparatus, the wells of a microtitration plate, a particle, a gel etc.

In one embodiment of the invention, the sample is also brought into contact with at least one chimeric fusion protein selected from those described below:

(a) a protein of which the amino acid sequence comprises (or consists of) the sequence SEQ ID NO: 25 and the sequence SEQ ID NO: 26 or a sequence which exhibits at least 40% identity with SEQ ID NO: 25 and a sequence which exhibits at least 50% identity with SEQ ID NO: 26, (b) a protein of which the amino acid sequence comprises (or consists of) the sequence SEQ ID NO: 27 and the sequence SEQ ID NO: 28 or a sequence which exhibits at least 40% identity with SEQ ID NO: 27 and a sequence which exhibits at least 50% identity with SEQ ID NO: 28, (c) a protein of which the amino acid sequence comprises (or consists of) a sequence selected from:

(i) the sequence SEQ ID NO: 29 and the sequence SEQ ID NO: 31 or a sequence which exhibits at least 40% identity with SEQ ID NO: 29 and a sequence which exhibits at least 50% identity with SEQ ID NO: 31, (ii) the sequence SEQ ID NO: 30 and the sequence SEQ ID NO: 31 or a sequence which exhibits at least 40% identity with SEQ ID NO: 30 and a sequence which exhibits at least 50% identity with SEQ ID NO: 31, (iii) the sequence SEQ ID NO: 29, the sequence SEQ ID NO: 30 and the sequence SEQ ID NO: 31, or a sequence which exhibits at least 40% identity with SEQ ID NO: 29, a sequence which exhibits at least 40% identity with SEQ ID NO: 30 and a sequence which exhibits at least 50% identity with SEQ ID NO: 31, (d) a protein of which the amino acid sequence comprises (or consists of) a sequence selected from SEQ ID NOs: 32, 34, 36 or a sequence selected from SEQ ID NOs: 33, 35, 37 and 38 described in greater detail below.

Each of the proteins identified above comprises at least one sequence of the extracellular domain of a DbpA protein of a *Borrelia* species selected from *B. afzelii* (SEQ ID NO: 25), *B. burgdorferi* sensu stricto (SEQ ID NO: 27) and *B. garinii* (group III: SEQ ID NO: 29) (group IV: SEQ ID NO: 30) or a sequence exhibiting at least 40% identity with said sequences, and at least one sequence of an OspC protein of *B. afzelii* (SEQ ID NO: 26), *B. burgdorferi* sensu stricto (SEQ ID NO: 28) and *B. garinii* (SEQ ID NO: 31) or a sequence which exhibits at least 50% identity with said sequences. Preferentially, the DbpA sequence(s) is (are) placed on the N-terminal side of the recombinant protein and the OspC sequence is placed on the C-terminal side of the recombinant protein.

As described previously, a sequence of at least 6 histidines can be added at the N-terminal or C-terminal end of the protein in order to enable its purification on metal-chelate resin. The 6-histidine sequence, identified in SEQ ID NO: 10, is preferentially placed on the N-terminal side of the construct. Additional amino acids may be present upstream of the poly-His tail owing to the insertion, into the coding DNA sequence, of a small sequence which makes it possible to facilitate the cloning of the sequence of interest into the expression plasmid, for example the "MRGS" motif (SEQ ID NO: 14) encoded by ATGAGGGGATCC (SEQ ID NO: 15).

A linking region can be introduced between each of the DbpA and OspC sequences which makes up a chimeric recombinant protein. This type of region corresponds to a flexible spacing region providing better accessibility of the potential antibodies to each of the domains. It is generally rich in Gly and Ser amino acids, which are amino acids described as providing flexibility in the tertiary structure of the protein. It is also possible to introduce, into a coding sequence of interest, a DNA arm (or linker) in order to promote the linking between the coding sequences for two proteins of interest. This is, for example, the "GSGG" motif (SEQ ID NO: 46) encoded by sequence GGTTCCGGGGGT (SEQ ID NO: 47), which acts as a linker arm between the DbpA group IV and OspC proteins of *B. garinii.*

Examples of these proteins are represented by SEQ ID NOs: 33, 35, 37 and 38 in the sequence listing.

The proteins described above and identified as SEQ ID NOs: 32 to 38 in the sequence listing are respectively encoded by the corresponding DNA sequences identified in SEQ ID NOs: 39 to 45.

The subject of the invention is also a kit for the in vitro diagnosis of Lyme borreliosis comprising at least one VlsE chimera protein as described above and optionally at least one DbpA/OspC chimeric fusion protein as defined previously, and preferably comprising at least one anti-human-immunoglobulin labeled with any appropriate label corresponding to the definitions given previously.

EXAMPLES

Example 1

Preparation of Plasmid Constructs Encoding the VlsE Chimeric Recombinant Proteins The DNA sequences encoding the various sequences of the protein are identified in table 1.

TABLE 1

| | Sequence origin | | |
|---|---|---|---|
| | *B. burgdorferi* species<br>*Isolate; **amino acids (aa); ***GenBank accession No. | | |
| protein | *B.* sensu stricto | *B. afzelii* | *B. garinii* |
| VlsE | — | — | *PBi; **aa 20-293; ***AJ630106 (GenScript Corp) |
| IR6 | *B31; **aa 274-305; ***U76405 (GeneArt GmbH) | *ACA-1; **aa 172-188; ***U76405 (GeneArt GmbH) | *Ip90; **aa 167-191; ***AAN87834 (GeneArt GmbH) |

The sequences were optimized for their expression in *E. coli* using GeneOptimizer™ and synthesized respectively by GenScript corporation (Scotch Plains, N.J., USA) or GeneArt GmbH (Regensburg, Germany).

Additional modifications to the DNA, deletions or combinations of various sequences were carried out by PCR by genetic engineering using the PCR techniques well known to those skilled in the art and described, for example, in Sambrook J. et al., Molecular Cloning: A Laboratory Manual, 1989. The DNA sequences were ligated into the pMR [2] or pET-3d (Novagen®) expression vector. The plasmid constructs and the corresponding proteins cited as example (bLYM110, bLYM125) are described in table 2.

TABLE 2

| Plasmid constructs and corresponding proteins | | | | |
|---|---|---|---|---|
| Recombinant protein characteristics | | | Plasmid construct characteristics | |
| Name | N-terminal Tag | *B. burgdorferi* sequence | Parental vector | Site of insertion of the insert sequence into the vector |
| bLYM110 SEQ ID NO: 21 | 6 x His | VlsE *garinii* pBi aa 20-293 + 3 IR6 [sensu stricto B21 aa 274-305 + *afzelii* ADA-laa 172-188 + *garinii* Ip90 aa 167-191] | pMR78 | 5'BamHI/3'HindIII |
| bLYM125 SEQ ID NO: 23 | 8 x His | | pET-3d | 5'NcoI/3'BamHI |

Example 2

Expression of the Recombinant Proteins of Example 1 and Purification

A plasmid construct described in example 1 was used to transform an *E. coli* bacterium (strain BL21) according to a conventional protocol known to those skilled in the art. The transformed bacteria were selected by virtue of their ampicillin resistance carried by the pMR or pET vector.

A clone of a recombinant bacterium was then selected in order to inoculate a preculture of 40 ml of 2×YT medium (16 g/1 tryptone; 10 g/1 yeast extract; 5 g/1 NaCl, pH 7.0) containing 100 μg/ml ampicillin. After 15 to 18 hours of incubation at 30° C. with shaking at 250 rpm, this preculture was used to inoculate 1 liter of 2×YT medium containing 2% glucose and 100 μg/ml ampicillin. This culture was incubated at 30° C. with shaking at 250 rpm until the OD at 600 nm reaches 1.0/1.2. The culture was maintained for 3 hours 30 min. or 4 hours at 30° C. while adding 0.4 mM isopropyl-β-D-thiogalactopyranoside (IPTG) and harvested by centrifugation at 6000 g for 30 min. The cell pellet was stored at −60° C. For the purification, the wet biomass was resuspended in a lysis buffer containing protease inhibitors without EDTA (Roche) and benzonase nuclease (Novagen®), and subjected to cell rupture at 1.6 kBar in a cell disrupter (Constant Systems Ltd, Daventry, United Kingdom). The lysate was then centrifuged at 10 000 rpm for 45 minutes at 2-8° C. After filtration through a 0.22 μm filter, the supernatant was loaded onto an Ni-NTA column (Qiagen®) equilibrated in a lysis buffer. The resin was then washed with the same buffer until the $A_{280\ nm}$ reached the base line. An elution was carried out with the elution buffer, and the purified protein was dialyzed in a Pierce Slide-A-Lyser® 10000 or 20000 MWCO dialysis cassette against the dialysis buffer. The conditions for purification on Ni-NTA gel are described in table 3.

TABLE 3

| Recombinant protein purification | | |
|---|---|---|
| Protein | bLYM110 SEQ ID NO: 21 | bLYM125 SEQ ID NO: 23 |
| Lysis and washing buffer | Buffer A[1] | Buffer A[1] + 2M urea |
| Elution buffer | Buffer B[2] | Buffer B[2] modified with 600 mM imidazole |
| Elution step 1 | 86% Buffer A + 14% Buffer B (4CV) | 92% Buffer A + 8% Buffer B (4CV) |
| Elution step 2 | 100% Buffer B | 100% Buffer B |
| Purification yield mg protein/g wet biomass | 0.5 | .8 |
| Purification yield mg protein/L of culture | 8.7 | 17 |

[1]50 mM sodium phosphate, 30 mM imidazole, 500 mM NaCl, 0.1% Tween 20, 5% glycerol, pH = 7.8

[2]50 mM sodium phosphate, 325 mM imidazole, 500 mM NaCl, 5% glycerol, pH = 7.5

The samples were analyzed on NuPAGE® Novex® 4-12% in a NuPAGE® MES-SDS circulating buffer, according to the instructions of the producer (Invitrogen™). The proteins were either stained with Coomassie brilliant blue or were transferred electrophoretically onto a nitrocellulose membrane. The membrane was blocked with 5% (w/v) dry milk in PBS and incubated with an anti-pentahistidine antibody (Qiagen®) in PBS containing 0.05% Tween 20. A horseradish peroxidase-labeled goat anti-mouse IgG conjugate (Jackson Immunoresearch laboratories) in PBS/Tween was used as secondary antibody.

The protein concentration was determined using the Bradford Assay Kit (Pierce Coomassie Plus, Perbio Science) with BSA as protein standard.

Example 3

Detection of Human IgGs and IgMs with the Chimeric Recombinant Protein bLYM110 of Example 2 Using a Line Immunoblot Technique The recombinant protein was deposited onto a polyvinylidene difluoride membrane (PVDF, Immobilon, Millipore®, Bedford, Mass. USA) according to the following protocol:

The protein concentration was adjusted to 1 mg/ml in PBS, pH 7.2, and diluted in PBS, pH 7.2, supplemented with 0.03% Tween 20 (dilution 1/200$^{th}$). The PVDF membrane was wetted in methanol, washed in demineralized water and laid out on a wet blotting paper. A plastic ruler was immersed in the protein dilution and attached to the PVDF membrane. After depositing of the proteins and drying of the membranes, the membranes were cut vertically into narrow strips. Before use, the narrow strips were incubated with 5% gelatin in TBS, pH 7.5, for 1 hour at 37° C. The immunoblot protocols were carried out at ambient temperature as described by Bretz A. G. et al. [3]. The narrow strips were incubated for 2 hours with human sera diluted to $1/200^{th}$ in TBS with 1% gelatin, washed and incubated with anti-human IgGs or IgMs labeled with alkaline phosphatase (Sigma™, St-Louis, USA) diluted to $1/1000^{th}$ in TBS with 1% gelatin. After washing, the narrow strips were incubated with the BCIP-NBT substrate (KPL, Gaithersburg, Md., USA) for 30 minutes, washed in distilled water and dried.

Panel of Sera Tested

The human sera were collected from clinically well-defined, typical LB patients corresponding to the various stages of LB (22 with erythema migrans [EM], 5 with carditis, 20 with neuroborreliosis [NB], 20 with Lyme arthritis [LA], 20 with acrodermatitis chronica atrophicans [ACA] and 10 with lymphadenosis cutis benigna [LCB]). Anti-Lyme IgGs were found by immunoblot, described previously using whole cell lysates [4], in the sera of patients with LA, ACA and carditis. EM, NB and LCB were identified clinically, but not all the corresponding sera were found to be positive using the immunoblot [4], or using the commercially available kits (Vidas® Lyme (Biomérieux®), *Borrelia* IgG (Diasorin®) and *Borrelia* IgM (r-Biopharm®)). On the other hand, all the cases of NB included in the study had detectable antibodies in the cerebrospinal fluid [CSF] (index extending from 2 to 27.1).

The negative control group consisted of 31 sera previously found to be negative for the presence of anti-Lyme antibodies in conventional assays. Furthermore, 64 sera from healthy blood donors residing in a region endemic for Lyme disease (Monthley, Valis, Switzerland) were tested with the recombinant protein. The strength of the reaction was evaluated as follows: [+], [++], [+++], [−] or equivocal results. The equivocal results were considered to be negative.

The results are given in table 4 below.

IgG Detection

The results indicate that the recombinant protein bLYM110 is a diagnostic antigen that is highly sensitive at all stages of the infection for IgGs. At stage I of the infection, the IgGs were detected in 17 cases of patients with EM out of 22 (i.e. 77.3% sensitivity). Five of the patients with EM who are found to be negative with the recombinant protein are also found to be negative with the in-house immunoblot and with the commercially available kits. Seven EM sera found to be positive with the recombinant protein were not detected by immunoblot, which represents a 31.8% improvement in sensitivity with the recombinant protein. At the primary stage of the infection, in the absence of characteristic redness, the diagnosis can be difficult since the other clinical manifestations of Lyme disease are not specific. Furthermore, only a few patients with EM are detected using the conventional tests. Therefore, the protein of the invention improves the detection of IgGs at stage I of the infection, bringing their detection to more than 77% in patients with EM.

IgM Detection

Anti-chimera protein IgMs are found in 23.4% of the LB sera. The protein detects the IgGs more often than the IgMs in the sera of stage-I and -II LB patients.

Example 4

Preparation of the Plasmid Constructs Encoding the DpbA-OspC Chimeric Recombinant Proteins The DNA sequences encoding the various DpbA and OspC sequences described are identified in table 5. The DNA sequences were optimized in order to promote expression in *E. coli* using GeneOptimizer™ and synthesized respectively by GenScript corporation (Scotch Plains, N.J., USA) or GeneArt GmbH (Regensburg, Germany).

TABLE 4

| IgG | | | | | | |
|---|---|---|---|---|---|---|
| Stage I | Stage II | | Stage III | | | Donors |
| EM (n = 22) | NB (n = 20) | Carditis (n = 5) | LA (n = 19) | ACA (n = 20) | Lymph. (n = 10) | (n = 64) |
| 17 | 20 | 5 | 19 | 20 | 9 | 6 |
| 77.3% | 100% | 100% | 100% | 100% | 90% | 9.4% |
| 12 [+++] | 11 [+++] | 4 [+++] | 13 [+++] | 20 [+++] | 3 [+++] | 6 [+] |
| 4 [++] | 7 [++] | 1 [++] | 4 [++] | | 2 [++] | |
| 1 [+] | 2 [+] | | 2 [+] | | 4 [+] | |
| Total IgG positives 93.7% | | | | | | |
| IgM | | | | | | |
| EM (n = 22) | NB (n = 20) | Carditis (n = 5) | | | | (n = 64) |
| 5 | 4 | 2 | | | | 1 |
| 22% | 20% | 40% | | | | 1.5% |
| 1 [++] | 2 [++] | 1 [++] | | | | 1 [+] |
| 4 [+] | 1 [+] | 1 [++] | | | | |
| Total IgM positives 23.4% | | | | | | |

TABLE 5

| Sequence origin | | | |
|---|---|---|---|
| | *B. burgdorferi* species<br>*Isolate; **amino acids (aa);<br>***GenBank accession No. | | |
| protein | *B.* sensu stricto | *B. afzelii* | *B. garinii* |
| DbpA | *B31; **aa 2-192;<br>***AF069269 | *PKo; **aa 2-150;<br>***AJ131967 | *40; **aa 2-187;<br>***AF441832<br>*PBi; **aa 2-176;<br>***AJ841673 |
| OspC | *B31; **aa 26-210;<br>***X73622 | *PKo; **aa 2-212;<br>***X62162 | *PEi; **aa 32-208;<br>***AJ749866 |

A poly-His sequence (6× histidine) was introduced on the N-terminal side of each recombinant protein. This sequence allows purification of the recombinant proteins on a metal-chelate affinity column. It is a region for attachment to the Ni-NTA gel which makes it possible to subsequently facilitate the step of purifying the chimeric recombinant protein. This HHHHHH peptide (SEQ ID NO: 10) is encoded by the nucleotide sequences CATCATCATCATCATCAT (SEQ ID NO: 11) or CATCATCATCATCATCAC (SEQ ID NO: 12) or CATCATCACCACCATCAT (SEQ ID NO: 13) or by any other sequence encoding the sequence SEQ ID NO: 10.

By way of indication, this particular attachment region, comprising a succession of histidines, allows in particular the oriented attachment of the recombinant protein to a support consisting of silica or of metal oxides.

TABLE 6

| Plasmid constructs and corresponding proteins | | | | | |
|---|---|---|---|---|---|
| Recombinant protein characteristics | | | Plasmid construct characteristics | | |
| Name | N-terminal Tag | *B. burgdorferi* sequence | name | Parental vector | Site of insertion of the insert sequence into the vector |
| bLYM114<br>SEQ ID<br>NO: 33 | 6 x His | *B. afzelii* strain PKo<br>DbpA aa 2-150 +<br>OspC aa 2-212 | pOL114 | pMR78* | 5'BamHI/3'EcoRI |
| bLYM120<br>SEQ ID<br>NO: 35 | 6 x His | *B.* sensu stricto strain B31<br>DbpA aa 28-192 +<br>OspC aa 26-210 | pOL120 | pMR78* | 5'BamHI/3'HindIII |
| bLYM121<br>SEQ ID<br>NO: 38 | 6 x His | *B. garinii*<br>DbpA III aa 25-187 strain<br>40 + DbpA IV aa 24-176<br>strain PBi +<br>OspC aa 32-208 strain PEi | pOL121 | pMR78* | 5'BamHI/3'HindIII |

Each chimeric recombinant protein comprises at least one epitope region corresponding to the extracellular domain of a DbpA sequence of *Borrelia burgdorferi* sensu stricto or *B. afzelii* or *B. garinii* and at least one epitope region corresponding to the extracellular domain of an OspC sequence of *Borrelia burgdorferi* sensu stricto or *B. afzelii* or *B. garinii.*

The combinations of various nucleotide sequences encoding DbpA and/or OspC sequences and also the modifications of nucleotide sequences, such as deletions, addition of a linking sequence or addition of a linker sequence, were carried out by genetic engineering using the PCR techniques well known to those skilled in the art and described, for example, in Sambrook J. et al., Molecular Cloning: A Laboratory Manual, 1989.

The DNA sequences encoding the chimeric proteins of interest were introduced into the pMR expression vector [2] between the BamHI restriction site in the 5' position and the EcoRI or HindIII site in the 3' position. The plasmid constructs and the corresponding proteins cited as example (bLYM114, bLYM120 and bLYM121) are described in table 6. The presence of MRGS in the N-terminal position of the recombinant proteins and the corresponding nucleotide sequence ATG AGG GGA TCC was introduced by the cloning technique used into the pMR expression vector. Only the ATG start codon and consequently the Met amino acid are really essential in this sequence.

Example 5

Expression of the Recombinant Proteins bLYM114, bLYM120 and bLYM121 of Example 4 and Purification A plasmid construct in which a sequence SEQ ID NO: 40, 42 or 45 has been inserted into an expression vector (pMR) was used to transform an *E. coli* bacterium (strain BL21) according to a conventional protocol known to those skilled in the art. The transformed bacteria were selected by virtue of their ampicillin resistance carried by the pMR vector.

A clone of a recombinant bacterium was then selected in order to inoculate a preculture of 40 ml of 2×YT medium (16 g/1 tryptone; 10 g/1 yeast extract; 5 g/1 NaCl, pH 7.0) containing 100 μg/ml of ampicillin. After 15 to 18 hours of incubation at 30° C. with shaking at 250 rpm, this preculture was used to inoculate 1 liter of 2×YT medium containing 2% glucose and 100 μg/ml of ampicillin. This culture was incubated at 30° C. with shaking at 250 rpm until the OD at 600 nm reaches 1.0/1.2. The culture was maintained for 3 hours 30 min. or 4 hours at 30° C. while adding 0.4 mM isopropyl-β-D-thiogalactopyranoside (IPTG), and harvested by centrifugation at 6000 g for 30 min. The cell pellet was stored at −60° C. For the purification, the wet biomass was thawed and resuspended in a lysis buffer containing protease inhibitors without EDTA (Roche™) and benzonase nuclease (Novagen), and subjected to cell rupture at 1.6 kBar in a cell disrupter (Constant Systems Ltd, Daventry, United Kingdom). The lysate was then centrifuged at 10 000 rpm for 45 min. at 2-8° C. The supernatant obtained contains the soluble proteins. This supernatant was filtered through a 0.45μ filter and purified by affinity chromatography on a metal chelation column (nickel-nitrilotriacetic acid matrix (Ni-NTA, Qiagen)). To do this, the supernatant was loaded (1 ml/min) at 18-25° C. onto an 8 ml column of Ni-NTA gel equilibrated in buffer A (see table 7). The column was then washed in buffer A, until an $OD_{280\ nm}$=0 was obtained at the column outlet. The elution of the recombinant protein is obtained by applying a buffer B, according to the indications reported in table 7, and the purified protein was dialyzed in a 10000 or 20000 MWCO dialysis cassette (Slide-A-Lyser®, Pierce) against a dialysis buffer. The conditions for purification on Ni-NTA gel are described in table 7.

TABLE 7

| Recombinant protein purification | | | |
|---|---|---|---|
| Protein | bLYM114 | bLYM120 | bLYM121 |
| Lysis and washing buffer | Buffer A[1] | | |
| Elution buffer | Buffer B[2] | | |
| Elution step 1 | 90% Buffer A + 10% Buffer B (4CV) | 92% Buffer A + 8% Buffer B (4CV) | 100% Buffer B |
| Elution step 2 | 100% Buffer B | 100% Buffer B | NA |
| Purification yield mg protein/g wet biomass | 12 | 13 | 20 |
| Purification yield mg protein/L of culture | 80 | 122 | 245 |

[1] 50 mM sodium phosphate, 30 mM imidazole, 500 mM NaCl, 0.1% Tween 20, 5% glycerol, pH = 7.8

[2] 50 mM sodium phosphate, 325 mM imidazole, 500 mM NaCl, 5% glycerol, pH = 7.5

The samples were analyzed on NuPAGE® Novex® 4-12% in a NuPAGE® MES-SDS buffer, according to the instructions of the producer (Invitrogen). The proteins were either stained with Coomassie brilliant blue or were transferred electrophoretically onto a nitrocellulose membrane. The membrane was blocked with 5% (w/v) dry milk in PBS and incubated with an antipentahistidine antibody (Qiagen®) in PBS containing 0.05% Tween 20. A horseradish peroxidase-labeled goat anti-mouse IgG conjugate (Jackson Immunoresearch laboratories) in PBS/Tween was used as secondary antibody.

The protein concentration was determined using the Bradford kit (Pierce Coomassie Plus, Perbio Science) with BSA as protein standard.

Example 6

Detection of Human IgGs and IgMs with the Chimeric Recombinant Proteins Using a Line Immunoblot Technique Each recombinant protein was deposited on a polyvinylidene difluoride membrane (PVDF, Immobilon, Millipore, Bedford, Mass. USA) according to the following protocol: The protein concentration was adjusted to 1 mg/ml in PBS, pH 7.2, and diluted in PBS, pH 7.2, supplemented with 0.03% Tween 20 (dilution $1/200^{th}$). The PVDF membrane was wetted in methanol, washed in demineralized water and laid out on a wet blotting paper. A plastic ruler was immersed in the protein dilution and attached to the PVDF membrane. After depositing of the proteins and drying of the membranes, the membranes were cut vertically into narrow strips. Before use, the narrow strips were incubated with 5% gelatin in TES, pH 7.5, for 1 hour at 37° C. The immunoblot protocols were carried out at ambient temperature as described by Bretz A. G. et al. [3]. The narrow strips were incubated for 2 hours with human sera diluted to $1/200^{th}$ in TBS with 1% gelatin, washed and incubated with an anti-human-IgG or anti-human-IgM antibody labeled with alkaline phosphatase (Sigma, St-Louis, USA) diluted to $1/1000^{th}$ in TBS with 1% gelatin. After washing, the narrow strips were incubated with the alkaline phosphatase substrate BCIP-NBT (KPL, Gaithersburg, Md., USA) for 30 min., and then washed in distilled water and dried.

Panel of Sera Tested

The human sera were collected from clinically well-defined, typical LB patients corresponding to the various stages of LB (22 with erythema migrans [EM], 5 with carditis, 20 with neuroborreliosis [NB], 20 with Lyme arthritis [LA], 20 with acrodermatitis chronica atrophicans [ACA] and 10 with lymphadenosis cutis benigna [LCB]). Anti-Lyme IgGs were found by immunoblot, using whole cell lysates [4], in the sera of patients with LA, ACA and carditis. EM, NB and LCB were identified clinically, but not all the corresponding sera were found to be positive by immunoblot [4], or using the commercially available kits (Vidas® Lyme (biomérieux), *Borrelia* IgG (Diasorin®) and *Borrelia* IgM (r-Biopharm®)). On the other hand, all the cases of NB included in the study had detectable antibodies in the cerebrospinal fluid [CSF] (index extending from 2 to 27.1 with Vidas® Lyme (biomérieux)). The presence of IgM was sought only in the stage I and stage II clinical cases and not in the chronic stages.

The negative control group consisted of 31 sera previously found to be negative for the presence of anti-Lyme antibodies in conventional assays. Furthermore, 64 sera from healthy blood donors residing in a region endemic for Lyme disease (Monthley, Valais, Switzerland) were tested with the recombinant protein.

The strength of the reaction was evaluated as follows: [+], [++], [+++], [−] or equivocal results. The equivocal results were considered to be negative.

The results are given in table 8 below.

TABLE 8

| Reactivity in Line immunoblot of human sera from patients with Lyme borreliosis, with 3 chimeric recombinant proteins | | | | | | | | | |
|---|---|---|---|---|---|---|---|---|---|
| | IgG | | | | | | IgM | | |
| | Stage I | Stage II | | Stage III | | | Stage I | Stage II | |
| Recombinant protein | EM (n = 22) | NB (n = 20) | Carditis (n = 5) | LA (n = 19) | ACA (n = 20) | LCB (n = 10) | EM (n = 22) | NB (n = 20) | Carditis (n = 5) |
| bLYM114 | 5 | 10 | 0 | 7 | 12 | 2 | 7 | 7 | 2 |
| bLYM120 | 6 | 7 | 0 | 8 | 6 | 0 | 11 | 7 | 2 |

TABLE 8-continued

Reactivity in Line immunoblot of human sera from patients with Lyme borreliosis, with 3 chimeric recombinant proteins

| | IgG | | | | | | IgM | | |
|---|---|---|---|---|---|---|---|---|---|
| | Stage I | Stage II | | Stage III | | | Stage I | Stage II | |
| Recombinant protein | EM (n = 22) | NB (n = 20) | Carditis (n = 5) | LA (n = 19) | ACA (n = 20) | LCB (n = 10) | EM (n = 22) | NB (n = 20) | Carditis (n = 5) |
| bLYM121 | 2 | 10 | 5 | 9 | 8 | 0 | 7 | 7 | 2 |
| Σ bLYM 114 + 120 + 121 | 9 | 13 | 5 | 18 | 17 | 2 | 11 | 7 | 2 |
| Positive sera (%) and reaction strength | 40.9%<br>1 [+++]<br>4 [++]<br>4 [+] | 59.1%<br>8 [+++]<br>2 [++]<br>3 [+] | 100%<br>4 [+++]<br>1 [+] | 94.7%<br>7 [+++]<br>8 [++]<br>3 [+] | 85%<br>8 [+++]<br>5 [++]<br>4 [+] | 20%<br>1 [++]<br>1 [+] | 50%<br>1 [+++]<br>7 [++]<br>5 [+] | 35%<br>5 [++]<br>2 [+] | 40%<br>2 [++] |
| Total positives and reaction strength | 66.7% | | | 28 [+++]<br>20 [++]<br>16 [+] | | | 42.5% | 1 [+++]<br>14 [++]<br>7 [+] | |

The specificity is 100% on the basis of 31 sera originating from healthy individuals determined to be Lyme-negative using the standard commercially available tests.

IgG Detection

The results indicate that the recombinant chimeric fusion proteins are diagnostic tools that are sensitive at all stages of the infection for IgGs and IgMs. They demonstrate an additional effect of the three recombinant proteins based, respectively, on sequences of *Borrelia afzelii, B. sensu stricto* and *B. garinii* for the detection of IgGs. The combined use of the three chimeric recombinant proteins makes it possible, at stage I of the infection, to detect IgGs in 9 cases of patients with EM out of 22 (i.e. 40.9% sensitivity).

IgM Detection

Anti-chimera protein IgMs are found in 11 cases out of 22 (i.e. 50% sensitivity). These chimera proteins therefore detect the IgMs more often than the IgGs in the sera of stage-I LB patients. The tests performed as a control: immunoblot [4], and commercially available kit *Borrelia* IgM (r-Biopharm®) do not further detect IgM-positive sera. In addition, 3 sera found to be negative using the immunoblot test and *Borrelia* IgM (r-Biopharm®) are detected by the three chimeric proteins cited as example (3/3) or by one of the three proteins cited as example (1/3). The combined use of the three recombinant proteins makes it possible to improve the IgM detection sensitivity by 13.6% in stage I of the infection.

Example 7

Evaluation and Validation of the Chimeric Recombinant Proteins bLYM114, bLYM120, bLYM121 and bLYM125 in a VIDAS® Test (bioMérieux)

This validation is carried out in a VIDAS® test using:

1) the recombinant chimeric proteins bLYM114, bLYM120 and bLYM121, obtained according to examples 4 and 5 for IgM detection, and 2) the chimeric recombinant proteins bLYM114 and bLYM120, obtained according to examples 4 and 5 and the chimeric protein bLYM125, obtained according to examples 1 and 2, for the IgG detection.

The principle of the VIDAS® test is the following: a tip constitutes the solid support which also serves as a pipetting system for the reagents present in the strip. The recombinant protein(s) is (are) attached to the tip. After a dilution step, the sample is drawn up and forced back several times in the tip. This allows the anti-Lyme immunoglobulins in the sample to bind to the recombinant proteins. The unbound proteins are removed by washing. An anti-human-immunoglobulin antibody conjugated to alkaline phosphatase (ALP) is incubated in the tip, where it binds to the anti-Lyme immunoglobulins. Washing steps remove the unbound conjugate. During the final visualizing step, the alkaline phosphatase (ALP) substrate, 4-methylumbelliferyl phosphate, is hydrolyzed to 4-methyl-umbelliferone, the fluorescence of which emitted at 450 nm is measured. The intensity of the fluorescence is measured by means of the Vidas® optical system and is proportional to the presence of anti-Lyme immunoglobulins present in the sample. The results are analyzed automatically by the VIDAS® and expressed as RFV (Relative Fluorescent Value).

255 positive sera (equivocal sera+positive sera) and 298 negative sera (equivocal+negative) were thus assayed with the Vidas® system.

The Vidas® Lyme IgG tips are sensitized with 300 μL of solution comprising the bLYM114, bLYM120 and bLYM125 proteins of the invention, each at a concentration of 1 μg/mL in a common sensitizing solution.

In the first step, the sera are incubated for 5.3 min. for the formation of the antigen-antibody complexes. In the second step, anti-human-IgGs labeled with ALP are incubated for 5.3 min.

The results are given as an index relative to a positivity threshold positioned at 135 RFV in the protocol.

Among the 255 positive sera tested, 246 are positive and 9 are falsely negative, which corresponds to a sensitivity of 96.5%.

Among the 298 negative sera tested, 284 are negative and 14 are falsely positive, which corresponds to a specificity of 95.3%.

LITERATURE REFERENCES

1. Göttner G. et al., Int. J. Microbiol. 293, Suppl. 37, 172-173 (2004)
2. Arnaud N. et al., Gene 1997; 199:149-156.
3. Bretz A. G., K. Ryffel, P. Hutter, E. Dayer and O. Péter. Specificities and sensitivities of four monoclonal antibodies for typing of *Borrelia burgdorferi* sensu lato isolates. Clin. Diag. Lab. Immunol. 2001; 8: 376-384.
4. Ryffel K., Péter O., Rutti B. and E. Dayer. Scored antibody reactivity by immunoblot suggests organotropism of *Borrelia burgdorferi* sensu stricto, *B. garinii, B. afzelii* and *B. valaisiana* in human. J. Clin. Microbiol. 1999; 37:4086-92
5. Steere A C. et al., Clin Infect Dis 2008; 47:188-195.

The invention claimed is:

1. A nucleic acid encoding a chimeric protein, the chimeric protein comprising:

(i) at least one amino acid sequence having at least 50% sequence identity with any of the amino acid sequences selected from the group consisting of SEQ ID NOS: 1-5; and (ii) at least one amino acid sequence having at least 80% sequence identity with any of the amino acid sequences selected from the group consisting of SEQ ID NOS: 6-8, wherein the chimeric protein comprises at least one amino acid sequence of (i) and at least one amino acid sequence of (ii) that are from different *Borrelia* strains or species.

2. The nucleic acid of claim 1, wherein the at least one amino acid sequence of (i) has at least 85% sequence identity with any of the amino acid sequences selected from the group consisting of SEQ ID NOS: 1-5, and the at least one amino acid sequence of (ii) has at least 85% sequence identity with any of the amino acid sequences selected from the group consisting of SEQ ID NOS: 6-8.

3. The nucleic acid of claim 1, wherein the chimeric protein further comprises a VR6 region of a *Borrelia* species.

4. The nucleic acid of claim 1, wherein the chimeric protein comprises:

an amino acid sequence having at least 50% sequence identity with the amino acid sequence of SEQ ID NO: 1;

an amino acid sequence having at least 80% sequence identity with the amino acid sequence of SEQ ID NO: 6;

an amino acid sequence having at least 80% sequence identity with the amino acid sequence of SEQ ID NO: 7; and an amino acid sequence having at least 80% sequence identity with the amino acid sequence of SEQ ID NO: 8.

5. The nucleic acid of claim 4, wherein the amino acid sequences have at least 85% sequence identity with the amino acid sequences of SEQ ID NOS: 1, 6, 7, and 8, respectively.

6. The nucleic acid of claim 4, wherein the chimeric protein further comprises the amino acid sequence of SEQ ID NO: 9.

7. The nucleic acid of claim 1, wherein the chimeric protein comprises the amino acid sequence of SEQ ID NO: 20, SEQ ID NO: 21, or SEQ ID NO: 23.

8. The nucleic acid of claim 7, comprising the nucleotide sequence of SEQ ID NO: 22 or SEQ ID NO: 24.

9. An expression cassette comprising the nucleic acid of claim 1 and elements for expressing the nucleic acid.

10. An expression cassette comprising the nucleic acid of claim 2 and elements for expressing the nucleic acid.

11. An expression cassette comprising the nucleic acid of claim 4 and elements for expressing the nucleic acid.

12. An expression cassette comprising the nucleic acid of claim 5 and elements for expressing the nucleic acid.

13. An expression cassette comprising the nucleic acid of claim 7 and elements for expressing the nucleic acid.

14. An expression cassette comprising the nucleic acid of claim 8 and elements for expressing the nucleic acid.

15. A vector comprising the expression cassette of claim 9.

16. A vector comprising the expression cassette of claim 10.

17. A vector comprising the expression cassette of claim 11.

18. A vector comprising the expression cassette of claim 12.

19. A vector comprising the expression cassette of claim 13.

20. A vector comprising the expression cassette of claim 14.

* * * * *